United States Patent
Schreiner et al.

(10) Patent No.: US 6,352,975 B1
(45) Date of Patent: Mar. 5, 2002

(54) METHODS OF TREATING HYPERTENSION AND COMPOSITIONS FOR USE THEREIN

(75) Inventors: George F. Schreiner, Los Altos Hills, CA (US); Richard J. Johnson, Seattle, WA (US)

(73) Assignee: Scios Inc., Sunnyvale, CA (US)

( * ) Notice: Subject to any disclaimer, the term of this patent is extended or adjusted under 35 U.S.C. 154(b) by 0 days.

(21) Appl. No.: 09/392,932

(22) Filed: Sep. 9, 1999

Related U.S. Application Data

(60) Provisional application No. 60/099,694, filed on Sep. 9, 1998, provisional application No. 60/126,406, filed on Mar. 26, 1999, and provisional application No. 60/126,615, filed on Mar. 27, 1999.

(51) Int. Cl.$^7$ ............... A61K 38/18; C07K 14/475; C07K 14/49
(52) U.S. Cl. ............... 514/12; 514/2; 530/399
(58) Field of Search ............... 514/2, 12; 530/399

(56) References Cited

U.S. PATENT DOCUMENTS

| | | |
|---|---|---|
| 4,456,550 A | 6/1984 | Dvorak et al. |
| 5,194,596 A | 3/1993 | Tischer et al. |
| 5,219,739 A | 6/1993 | Tischer et al. |
| 5,240,848 A | 8/1993 | Keck et al. |
| 5,332,671 A | 7/1994 | Ferrara et al. |

FOREIGN PATENT DOCUMENTS

| | | |
|---|---|---|
| EP | 0 464 155 B1 | 5/1997 |
| WO | WO 98/20027 | 5/1998 |

OTHER PUBLICATIONS

Johnson and Schreiner, *Kidney Int.* 52:1169–1179 (1998).
Johnson et al., *Hypertension* 19:464–474 (1992).
Roberts and Palade, *J. Cell Sci.* 108:2369–2379 (1995).
Esser et al., *J. Cell. Biol.* 140:947–959 (1998).
Kramer et al., *Kidney Int.* 51:444–447 (1997).
Shulman et al., *J. Am. Soc. Nephr.* 7:661–666 (1996).
Ferrara and Davis–Smyth, *Endocrine Rev.* 18:4–25 (1997).
Monacci et al., *Am. J. Physiol.* 264:C995–C1002 (1993).
Hariawala et al., *J. Surgical Res.* 63:77–82 (1996).
Sellke et al., *Am. J. Physiol.* 271:H713–H720 (1996).
Henry et al., *J. Am. Coll. Cardiol.* 32(2; Suppl. A):65A (1998).
Lombardi et al., *Hypertension* 33:1013–1019 (1999).
Klagsburn and D'Amore, *Cytokine and Growth Factor Reviews* 7:259–270 (1996).
Kaplan et al., *Pediatr. Nephrol.* 4:276 (1990).
Remuzzi and Ruggenti, *Kidney Int.*, 48:2–19 (1995).
Neilson and Couser eds., *Immunologic Renal Diseases*, Lippincott–Raven Philadelphia, 1996, pp. 1161–1181.
Habib et al, *Adv. Nephrol.* 11:99–128 (1982).
Nangaku et al., *Kidney Int.* 52:1570–1578 (1997).
Nangaku et al., *Kidney Int.* 52:182–194 (1997).
Nangaku et al., *Curr. Opin. Nephrol. Hypertens.* 7:457–462 (1998).
Gerber et al., *J. Biol. Chem.* 273:3–336–30343 (1998).
Spyridopoulos et al., *J. Mol. Cell Cardiol.* 29:1321–1330 (1997) [erratum published in *J. Mol. Cell Cardiol.* 30:897 (1998)].
Gerber et al., *Development* 126:1149–1159 (1999).
Takeshita et al., *J. Clin. Invest.* 93:662–670 (1994).
Iruela et al., *Am. J. Pathol.* 147:1715–1727 (1995).
Kitamura et al., *Exp. Nephrol.* 6:328–336 (1998).
Tuder et al., *J. Clin. Invest.* 95:1798–1807 (1995).
Banai et al., *Circulation* 89:2183–2189 (1994).
Alon et al., *Nat. Med* 1:1024–1028 (1995).
Benjamin et al., *J. Clin. Invest.* 103:159–165 (1999).
Papapetropoulos et al., *Clin. Invest.* 100:3131–3139 (1997).
Wu et al., *Am. J. Physiol.* 271:H2735–2739 (1996).
Ku et al., *Am. J. Physiol.* 265:H586–592 (1993).
Gordjani et al., *Semin. Thromb. Hemost.* 23:281–293 (1997).
Concepcion et al., (1998) Tissue availability of insulin–like growth factor I is inversely related to insulin resistance in essential hypertension: Effects of angiotensin converting enzyme inhihition. Journal of Hypertension. 16(6):863–870. Abstract. XP–002135130.
Voelkel et al. (1996) Vascular endothelial growth factor in pulmonary hypertension. Annals of the New York Academy of Sciences. 186–93.

*Primary Examiner*—Christine J. Saoud
(74) *Attorney, Agent, or Firm*—Knobbe Martens Olson & Bear LLP

(57) ABSTRACT

The present invention concerns methods for the treatment of salt-sensitive hypertension. The methods generally involve administering a vascular endothelial growth factor (VEGF) in an amount effective to reduce the blood pressure of a patient suffering from salt-sensitive hypertension to a normal range.

8 Claims, 11 Drawing Sheets hVEGF121

ATGAACTTTCTGCTGTCTTGGGTGCATTGGAGCCTTGCCTTGCTGTCTTACCTCCACCATGCCAA
GTGGTCCCAGGCTGCACCCATGGCAGAAGGAGGAGGGCAGAATCATCACGAAGTGGTGAAGTTCA
TGGATGTCTATCAGCGCAGCTACTGCCATCCAATCGAGACCCTGGTGGACATCTTCCAGGAGTAC
CCTGATGAGATCGAGTACATCTTCAAGCCATCCTGTGTGCCCCTGATGCGATGCGGGGCTGCTG
CAATGACGAGGGCCTGGAGTGTGTGCCCACTGAGGAGTCCAACATCACCATGCAGATTATGCGA
TCAAACCTCACCAAGGCCAGCACATAGGAGAGATGAGCTTCCTACAGCACAACAAATGTGAATGC
AGACCAAAAGAAAGATAGAGCAAGACAAGAAAAATGTGACAAGCCGAGGCGGTGA

MNFLLSWVHWSLALLLYLHHAKWSQAAPMAEGGGQNHHEVVKFMDVYQRSYCHPIETLVDIFQEY
PDEIEYIFKPSCVPLMRCGGCCNDEGLECVPTEESNITMQIMRIKPHQGQHIGEMSFLQHNKCEC
RPKKDRARQEKCDKPRR

FIG.6 hVEGF145

ATGAACTTTCTGCTGTCTTGGGTGGATTGGAGCCTTGCCTTGCTGTCTTACCTCCACCATGCCAAGTG
GTCCCAGGCTGCACCCATGGCAGAAGGAGGAGGGCAGAATCATCACGAAGTGGTGAAGTTCATGGAT
GTCTATCAGCGCAGCTACTGCCATCCAATCGAGACCCTGGTGGACATCTTCCAGGAGTACCCTGATGA
GATCGAGTACATCTTCAAGCCATCCTGTGTGCCCCTGATGCGATGCGGGGGCTGCTGCAATGACGAG
GGCCTGGAGTGTGTGCCCACTGAGGAGTCCAACATCACCATGCAGATTATGCGGATCAAACCTCACCA
AGGCCAGCACATAGGAGAGATGAGCTTCCTACAGCACAACAAATGTGAATGCAGACCAAAGAAAGATA
GAGCAAGACAAGAAAAAATCAGTTCGAGGAAAGGGAAAGGGCAAAAACGAAAGCCAAGAAATC
CCGGTATAAGTCCTGGAGCGTATGTGACAAGCCGAGGCGGTGA

APMAEGGGQNHHEVVKFMDVYQRSYCHPIETLVDIFQEYPDEIEYIFKPSCVPLMRCGGCCNDEG
LECVPTEESNITMQIMRIKPHQGQHIGEMSFLQHNKCECRPKKDRARQEKKSVRGKGKGQKRKRK
KSRYKSWSVCDKPRR

FIG.7

Hvegf 165

ATGAACTTTCTGCTGTCTTGGGTGCATTGGAGCCCTCGCCTTGCTGCTCTACCTCCACCATGCCAA
GTGGTCCCAGGCTGCACCCATGGCAGAGGAGGAGGGCAGAATCATCACGAAGTGGTGAAGTTCA
TGGATGTCTATCAGCGCAGCTACTGCCATCCAATCGAGACCCTGGTGGACATCTTCCAGGAGTAC
CCTGATGAGATCGAGTACATCTTCAAGCCATCCTGTGTGCCCCTGATGCGATGCGGGGCTGCTG
CAATGACGAGGGCCTGGAGTGTGTGCCCACTGGAGAGTGAGCTTCCTACAGCACAACAAATGTGAATGC
TCAAACCTCACCAAGGCCAGCACATAGAGAGCAAGAGAGAAAATCCCTGTGGCCTTGCTCAGAGCGGAGAAAGCA
AGACCAAAGAAGATAGAGCAAGACAAGACAAGAAATCCCTGTAAATGTTCCTGCAAAAACACAGACTCGCGTTGCAAGG
TTTGTTTGTACAAGATCCGCAGACGTGTAAATGTTCCTGCAAAAACACAGACTCGCGTTGCAAGG
CGAGGCAGCTTGAGTTAAACGAACTACTTGCAGATGTGACAAGCCGAGGCGGTGA

MNFLLSWVHWSLALLYLHHAKWSQAAPMAEGGGQNHHEVVKFMDVYQRSYCHPIETLVDIFQEY
PDEIEYIFKPSCVPLMRCGGCCNDEGLECVPTEESNITMQIMRIKPHQGQHIGEMSFLQHNKCEC
RPKKDRARQENPCGPCSERRKHLFVQDPQTCKCSCKNTDSRCKARQLELNERTCRCDKPRR.

FIG.8

Hvegf 189

ATGAACTTTCTGCTGTCTTGGGTGCATTGGAGCCCTCGCCTTGCTGCTCTACCTCCACCATGCCAA
GTGGTCCCAGGCTGCACCCATGGCAGAGGAGGAGGGCAGAATCATCACGAAGTGGTGAAGTTCA
TGGATGTCTATCAGCGCAGCTACTGCCATCCAATCGAGACCCTGGTGGACATCTTCCAGGAGTAC
CCTGATGAGATCGAGTACATCTTCAAGCCATCCTGTGTGCCCCTGATGCGATGCGGGGCTGCTG
CAATGACGAGGGCCTGGAGTGTGTGCCCACTGGAGAGTGAGCTTCCTACAGCACAACAAATGTGAATGC
TCAAACCTCACCAAGGCCAGCACATAGAGAGCAAGAGAGAAAATCCCTGTGGCCTTGCTCAGAGCGGAGAAAGGGCAAAA
AGACCAAAGAAGATAGAGCAAGACAAGACAAGAAATCAGTTCGGAGGAAAGGGAAAGGGCAAAA
ACGAAAGCCAAGAAATCCCGGTATAAGTCCTGGAGCCGTGGGCCTTGCTCAGAGCCGGAGAAAGC
ATTTGTTTGTACAAGATCCGCAGACGTGTAAATGTTCCTGCAAAAACACAGACTCGCGTTGCAAG
GCGAGGCAGCTTGAGTTAAACGAACTACTTGCAGATGTGACAAGCCGAGGCGGTGA

MNFLLSWVHWSLALLYLHHAKWSQAAPMAEGGGQNHHEVVKFMDVYQRSYCHPIETLVDIFQEY
PDEIEYIFKPSCVPLMRCGGCCNDEGLECVPTEESNITMQIMRIKPHQGQHIGEMSFLQHNKCEC
RPKKDRARQEKKSVRGKGKGQKRKRKKSRYKSWSVPCGPCSERRKHLFVQDPQTCKCSCKNTDSR
CKARQLELNERTCRCDKPRR

FIG.9

Hvegf 206

ATGAACTTTCTGCTGTCTTGGGTGCATTGGAGCCTCGCCCTTGCTGCTCTACCTCCACCATGCCAA
GTGGTCCCAGGCTGCACCATGGCAGAAGGAGGACAGAATCATCACGAAGTGGTGAAGTTCA
TGGATGTCTATCAGCGCAGCTACTGCCATCCAATCGAGACCCTGGTGGACATCTTCCAGGAGTAC
CCTGATGAGATCGAGTACATCTTCAAGCCATCCTGTGTGCCCCTGATGCGATGCGGGGCTGCTG
CAATGACGAGGGCCTGGAGTGTGTGCCCACATAGGAGAGATGAGCTTCCTACAGCACACAAATGTGAATGC
TCAAACCTCACCAAGGCCAGCACATAGGAGAGAAAAATCAGTTCGAGGAAAGGGAAGGGCAAAA
AGACCAAAGAAGATAGAGCAAGACAAGATTCCTGAGCGTTGTACGTTGGTGCCCGCTGCTCTAA
ACGAAAGCGCAAGAAATCCGGTATAAGTCCTGAGCGTGTAGTTGGTGCCCGCTGCTCTAA
TGCCCTGGAGCCTCCCTGGCCCCCATCCTGGGCCTTGCTCAGAGCGGGAGAAAGCATTTGTTT
GTACAAGATCCGCAGACGTGTAAATGTTCCTGCAAAACACAGACTCCGCGTTGCAAGGCGAGGCA
GCTTGAGTTAAACGAACTACTTGCAGATGTGACAAGCCGAGGCGGTGA

MNFLLSWVHWSLALLLYLHHAKWSQAAPMAEGGGQNHHEVVKFMDVYQRSYCHPIETLVDIFQEY
PDEIEYIFKPSCVPLMRCGGCCNDEGLECVPTEESNITMQIMRIKPHQGQHIGEMSFLQHNKCEC
RPKKDRARQEKKSVRGKGKGQKRKRKKSRYKSWSVYVGARCCLMPWSLPGPHPCGPCSERRKHLF
VQDPQTCKCSCKNTDSRCKARQLELNERTCRCDKPRR

FIG. 10

Hvegf110

APMAEGGGQNHHEVVKFMDVYQRSYCHPIETLVDIFQEYPDEIEYIFKPSCVPLMRCGGCCNDEG
LECVPTEESNITMQIMRIKPHQGQHIGEMSFLQHNKCECRPKKDR

FIG. 11

METHODS OF TREATING HYPERTENSION AND COMPOSITIONS FOR USE THEREIN

CROSS-REFERENCE TO RELATED APPLICATIONS

This is a non-provisional application of co-pending provisional application Serial No. 60/099,694 filed on Sep. 9, 1998; of provisional application Serial No. 60/126,406 filed Mar. 26, 1999; and of provisional application Serial No. 60/126,615 filed Mar. 27, 1999, the disclosures of which are hereby incorporated by reference and to which application priority is claimed under 35 USC 119.

TECHNICAL FIELD

The present invention relates to methods for treating hypertension, using a factor that stimulates angiogenesis and/or promotes vascular permeability.

BACKGROUND OF THE INVENTION

Systemic hypertension is the most prevalent cardiovascular disorder in the United States, affecting over 60 million Americans. In spite of increasing public awareness and a rapidly expanding array of antihypertensive medications, hypertension remains one of the leading causes of cardiovascular morbidity and mortality. Hypertension treatments have focused on stimulating the relaxation of the peripheral vasculature (vasodilation), depressing cardiac function, or by stimulating salt transport by blocking epithelial transport of sodium or chloride (diuresis). "Textbook of Medical Physiology", Guyton and Hall, eds. p. 234 (1996) W. B. Saunders. In addition, adverse metabolic effects have been observed with treatment using certain classes of antihypertensive treatment in coronary disease prevention. "Cecil Textbook of Medicine" pp. 252–269 (1992) W. B. Saunders. Therefore, there is a need to develop improved methods of treatment of hypertension.

Essential hypertension is the pathological expression of the inability to excrete a dietary sodium load efficiently. The causes for and the mechanism of the development of essentially hypertension are less than clear. According to one of the several possible theories, excreting a sodium load depends on the permeability of the vascular/epithelial barrier in the excreting organs such as the kidney and/or the surface area of the vascular/epithelial structures available for solute flux.

In tissues, the basement membrane serves to separate epithelial cells from blood vessels containing endothelial cells, particularly in the transport or flux of solutes in solution, such as sodium chloride, across basement membranes. Normally, the endothelium is relatively impermeable, limiting the flux of solutes and fluid across the basement membrane against which it is juxtaposed. However, the function of several specialized tissues requires permeable capillary beds to support solute flux. Such functions include the filtration of solutes by the kidney to regulate intravascular volume and maintain normal blood pressure, reabsorption of fluid secretions in the lungs to preserve pulmonary oxygenation, reabsorption of fluids containing solutes in the intestines to provide nutrition, production of cerebrospinal fluid in the choroid plexus of the brain to support and protect the central nervous system, diffusion of nutrients toward non-vascular tissue as occurs in certain portions of the eye or in wound healing, and reabsorption of interstitial fluid from the peritoneum. Impaired transport of solutes across basement membranes contributes to or exacerbates, among other disorders, essential hypertension, kidney disease, acute respiratory disease syndrome, macular ischemia, intestinal inflammatory diseases, meningitis, stroke, ascites, impaired peritoneal dialysis efficiency, and impaired wound healing.

A number of factors may potentially affect solute flux between the endothelial bed and epithelial tissue, including: (1) the metabolic activity of the epithelial cells of a particular tissue; (2) the number of the blood vessels adjacent to the epithelium and its basement membrane; and (3) the porosity or permeability of said blood vessels. Some of the diseases cited above are associated with epithelial cell toxicity, such as acute respiratory distress syndrome and kidney disease or with altered integrity of the capillary blood vessels, as occurs in vasculitis or ischemia. Other disease syndromes, such as essential hypertension have no defined central mechanism. The diseases cited above may be associated with diminished capillary number or altered porosity of the capillary vessel.

Angiogenesis, i.e. the growth of new capillary blood vessels, is a process which is crucial to normal tissue formation and repair. Consequently, factors that are capable of promoting angiogenesis are useful as wound healing agents. Angiogenesis is a multi-step process involving capillary endothelial cell proliferation, migration and tissue penetration. A number of known growth factors, including basic and acidic fibroblast growth factor, transforming growth factor α and epidermal growth factor, are broadly mitogenic for a variety of cell types as well as being angiogenic and are, therefore, potentially useful in promoting tissue repair. Broad spectrum mitogenicity is desirable in many types of tissue repair applications. There are, however, specific types of tissue repair applications in which it would be desirable to have endothelial cell-specific mitogenic activity, since proliferation of other cell types along with endothelial cells could cause blockage and/or reduced blood flow.

Vascular endothelial growth factor (VEGF) is a secreted endothelial cell mitogen that, when delivered in vivo, promotes new blood vessel formation. The VEGF protein consists of two polypeptide chains, linked by two disulfide bonds. Although the protein is generally described as a homodimer, heterodimeric species have also been reported. Through alternative splicing of the VEGF RNA transcript, five different forms of the monomer chain can be generated, extending 121, 145, 165, 189, and 206 amino acid residues in length. Tischer et al. (1991) *J. Biol. Chem.* 266:11947–11954; Houck et al. (1991) *Mol. Endocrinol.* 5:1806–1814; Charnock-Jones et al. (1993) *Biol. Reprod.* 48:1120–1128; and Neufeld et al. (1996) *Cancer Metastasis Rev.* 15:153–158. The 121-residue form of VEGF ($VEGF_{121}$) is unique among the five forms in that it does not bind to heparin-like molecules associated with the extracellular matrix. $VEGF_{121}$ and the 165-residue form, $VEGF_{165}$, appear to be the most prevalent forms in vivo.

VEGF is known to stimulate new blood vessel formation by stimulating endothelial cell proliferation and by inducing chemotaxis of endothelial cells. In contrast to other mitogens such as the fibroblast growth factors, VEGF has a much more restricted range of target cell type, and is mitogenic almost exclusively toward endothelial cells. VEGF is also known to enhance vascular permeability and can trigger the relaxation of blood vessels through the release of endothelial nitric oxide. Hariawala et al. (1996) *J Surgical Res.* 63:77–82; and Sellke et al. (1996) *Am. J. Physiol.* 271:H713–H720. In addition, VEGF has been shown to regulate the expression of other growth factors and biological mediators and may participate in a growth factor cascade that promotes tissue remodeling and repair.

The activity of VEGF is mediated by interaction with specific membrane receptors on target tissues, most notably the vascular endothelium. Both $VEGF_{121}$ and $VEGF_{165}$ are known to interact with two tyrosine kinase receptors: kinase insert domain-containing receptor (KDR; also known as Flk-1), and fms-like tyrosine kinase-1 (Flt-1). deVries et al. (1992) *Science* 255:989–991; Terman et al. (1992) *Biochem. Biophys. Res. Commun.* 187:1579–1586; and Millauer et al. (1993) *Cell* 72:835–846. Both KDR and Flt-1 consist of extracellular ligand-binding domains and intracellular tyrosine kinase domains, the latter being functionally activated upon engagement of VEGF. KDR is found only on endothelial cells, while Flt-1 is found on endothelial cells and monocytes. The angiogenic properties and other known functions of VEGF appear to be mediated via KDR and Flt-1.

Each human kidney comprises about one million nephrons, each capable of forming urine. Each nephron has two major components: a glomerulus, through which large amounts of fluid are filtered from the blood, and a long tubule, in which the filtered fluid is converted into urine. The glomerular capillary has three major layers: the endothelium, a basement membrane, and a layer of epithelial cells. The capillary endothelium is perforated by thousands of small holes called fenestrae.

VEGF can increase the permeability of blood vessels to solutes on a long-term basis by inducing the formation of fenestrations between endothelial cells. Roberts and Palade (1995) *J. Cell Sci.* 108:2369–2379; and Esser et al. (1998) *J. Cell Biol.* 140:947–959. In some tissues, such as the renal glomerulus, the glomerular epithelium is known to chronically secrete VEGF, presumably to maintain the fenestrations of the glomerular capillary endothelium. The solute ultrafiltrate that ultimately forms the urine produced by the kidney flows through these fenestrations. The choroid plexus in the brain responsible for producing cerebrospinal fluid and the distal tubule of the kidney, where sodium and potassium are exchanged for the final control of the urine solute concentration also contain fenestrated endothelium adjacent to VEGF-producing epithelium. Proper sodium and potassium exchange in the distal tubule is essential for the maintenance of normal intravascular volume.

Other epithelia known to constitutively produce VEGF include the epithelia of the lung, intestines, and skin. Ferrara and Davis-Smith (1997) *Endocrine Rev.* 18:4–25; and Monacci et al. (1993) *Am. J. Physiol.* 264:C995–C1002. Non-epithelial cells that make VEGF are fibroblasts and vascular smooth muscle cells, which secrete VEGF in response to tissue hypoxia, and thus stimulate the formation of new blood vessels. Ferrara and Davis-Smith (1997) *Endocrine Rev.* 18:4–25.

In contrast to the mesenchymal cells that produce VEGF, hypoxia does not appear to be a stimulus for VEGF production in epithelial cells. Specialized endothelia that express VEGF receptors in the absence of hypoxia include the glomerular and peritubular capillaries of the kidney, the capillaries of the choroid plexus, and endothelia in the intestines, lungs, retina, and heart valve. Little is known about modulation of VEGF secretion by epithelia. In the kidney, it is known that hypoxia is not a signal for VEGF secretion. Krämer et al. (1997) *Kidney International* 51:444–447.

SUMMARY OF THE INVENTION

The present invention provides methods of treating hypertension, particularly essential hypertension. The methods generally involve providing a stimulator of angiogenesis and/or of blood vessel porosity to maintain or correct the transport of solutes, including sodium chloride, and fluid across a basement membrane separating blood vessels or other vessels containing endothelium from epithelial cells. Such transport can be from the blood vessel across the basement membrane to or by the epithelial cells; or it can be from or by epithelia across the basement membrane to blood vessels. Stimulation of vessel number or porosity is used to increase the efficiency or extent of solute transport, thus decreasing blood volume and the concomitant hypertension.

In one aspect, the invention concerns a method for treating essential hypertension, comprising administering to a patient an effective amount of an angiogenic factor, or an agonist thereof. The angiogenic factor can be administered alone or in combination with a further anti-hypertensive agent, such as another angiogenic factor, and preferably is a vascular endothelial growth factor (VEGF) molecule.

The vascular endothelial growth factor is preferably selected from the group consisting of native hVEGF145 (FIG. 7, SEQ ID NO: 2), native hVEGF165 (FIG. 8, SEQ ID NO: 3), native hVEGF189 (FIG. 9, SEQ ID NO: 4), native hVEGF206 (FIG. 10, SEQ ID NO: 5), and agonists of any one of such native VEGF proteins.

In a particularly preferred embodiment, the VEGF molecule lacks the ability to bind heparin, and is, for example, hVEGF121.

The hypertension preferably is salt-dependent hypertension.

In another aspect, the invention concerns an article of manufacture comprising:

a container;

a composition comprising an angiogenic factor or an agonist thereof, in an amount effective in the treatment of hypertension; and instructions to administer the composition for the treatment of hypertension.

Again, the composition may contain an additional anti-hypertensive agent, e.g. a further angiogenic factor. The angiogenic factor preferably is a VEGF molecule or an agonist thereof.

In a further aspect, the invention concerns a method for identifying an anti-hypertensive agonist of a VEGF molecule comprising testing the ability of a candidate agonist to treat hypertension in a standard animal model of hypertension, in comparison with the VEGF molecule.

The invention further provides compositions for use is the foregoing methods and articles of manufacture. The compositions may contain one or more active ingredients, at least one of which is an angiogenic factor present in an amount effective in the treatment of hypertension. Alternatively, the compositions may comprise one or more polynucleotides comprising nucleotide sequences which encode an angiogenic factor, such as a VEGF, an polypeptide agonist of an angiogenic factor, or a polypeptide factor stimulating the production of an angiogenic factor.

BRIEF DESCRIPTION OF THE DRAWINGS

FIG. 4a: Rats in one group (solid diamonds) were fed a diet containing normal levels (0.1% w/w NaCl) of salt, while rats in a second group (open squares) were placed on a diet containing 4% (w/w) sodium chloride for three days. The vertical arrow indicates beginning of the high-salt diet. FIG. 4b: Rats fed the normal salt (solid diamonds) or high salt (open squares) diets, as shown in FIG. 4a, were treated with angiotensin II from days 0 to 14. The vertial arrow indicates discontinuation of Angiotensin II treatment. FIG. 4c: Rats on a high-salt diet were given VEGF for 14 days concurrent with a 7-day infusion of Angiotensin II (solid triangles), Angiotensin II alone (solid squares), or neither (solid diamonds). The vertical arrow indicates beginning of the VEGF and/or Angiotensin II treatment.

FIG. 6 shows the amino acid sequence (SEQ ID NO: 1) and the encoding nucleotide sequence (SEQ ID NO: 6) of native hVEGF121.

FIG. 7 shows the amino acid sequence (SEQ ID NO: 2) and the encoding nucleotide sequence (SEQ ID NO: 7) of native hVEGF 145.

FIG. 8 shows the amino acid sequence (SEQ ID NO: 3) and the encoding nucleotide sequence (SEQ ID NO: 8) of native hVEGF165.

FIG. 9 shows the amino acid sequence (SEQ ID NO: 4) and the encoding nucleotide sequence (SEQ ID NO: 9) of native hVEGF 189.

FIG. 10 shows the amino acid sequence (SEQ ID NO: 5) and the encoding nucleotide sequence (SEQ ID NO: 10) of native hVEGF206.

FIG. 11 shows the amino acid sequence (SEQ ID NO: 11) of native hVEGF110.

MODES OF CARRYING OUT THE INVENTION

Figure 1:
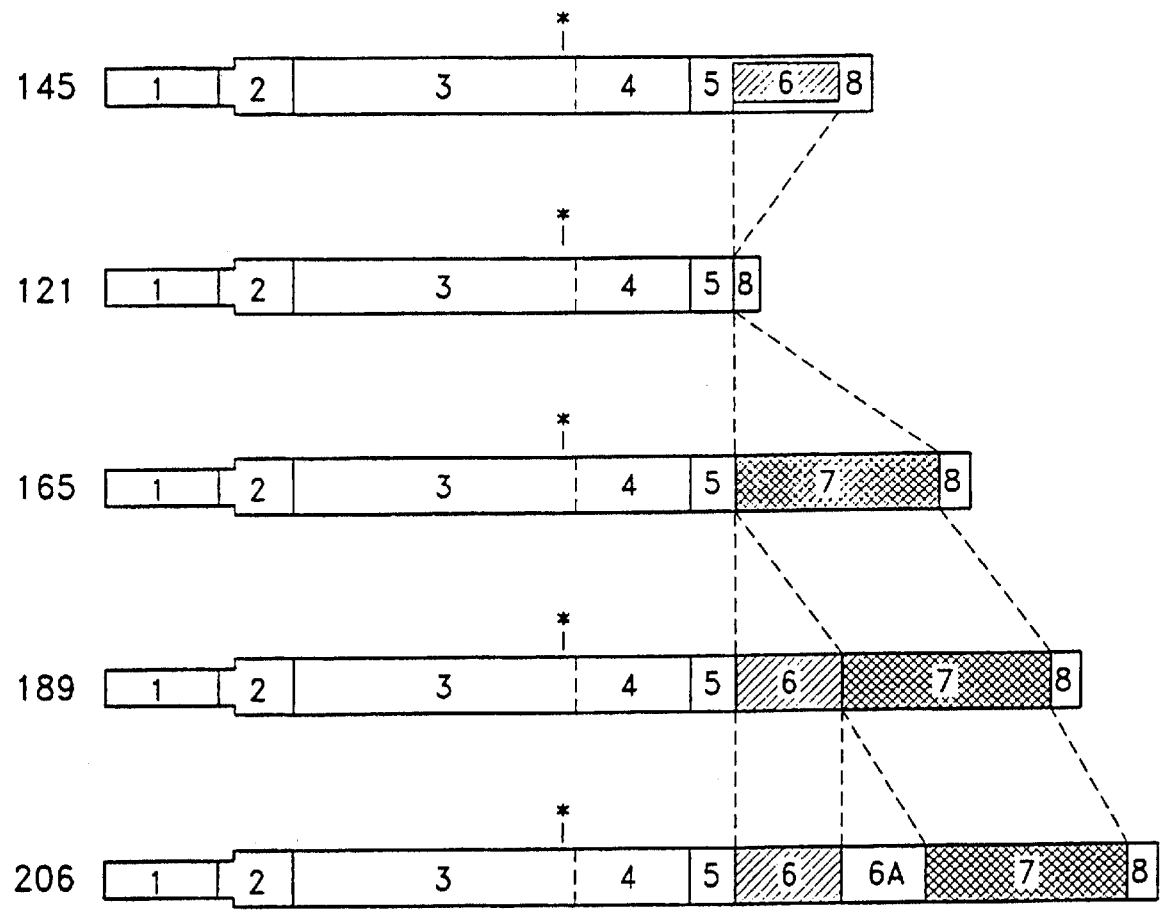
FIG. 1 is a schematic representation of the various forms of VEGF generated by alternative splicing of VEGF mRNA. The protein sequences encoded by each of the eight exons of the VEGF gene are represented by numbered boxes. The sequences encoded by exons 6 and 7 are rich in basic amino acid residues and confer the ability to interact with heparin and heparin-like molecules. Asterisks indicate N-linked glycosylation sites. Exon 1 and the first part of exon 2 (depicted by a narrower bar) encode the secretion signal sequence for the protein.

In animals and patients with essential hypertension, in the presence of diminished sodium chloride in the diet, the kidney is able to maintain a normal or near-normal blood pressure. The model system described herein creates salt-dependent hypertension in which transient exposure to a preceding hypertensive stimulus such as Angiotensin II (AII) or norepinephrine confers a susceptibility to hypertension which is dependent upon the amount of sodium chloride, or solute, in the diet, much like essential hypertension. Johnson and Schreiner (1997) *Kidney International* 52:1169–1179. As is the case with essential hypertension, kidneys with a preceding exposure to a transient or labile hypertensive stimulus are unable to handle the increased filtered load of solute arising from dietary exposure, with a consequent development of elevated blood pressure. Johnson and Schreiner (1997).

In most forms of kidney disease, renal production of VEGF is diminished. Shulman et al. (1996) *J. Am. Soc. Nephrol.* 7:661–666. Both VEGF and eNOS are constitutively co-localized to collecting ducts and medullary thick ascending limb tubular cells in the outer medulla of the rat. With acute vasoconstriction such as that induced by cyclosporine, an increase in both cortical hypoxia and VEGF expression can be documented, and is consistent with the known ability of hypoxia to induce VEGF expression. However, once chronic tubulointerstitial disease develops, our group has noted a loss of VEGF in the outer medulla, especially in the medullary thick ascending limb. This finding was observed not only in rats with cyclosporine induced nephropathy but also with the tubulointerstitial disease that accompanies aging, hypokalemia, and following angiotension II infusion.

Most forms of renal disease are also associated with hypertension, raising the possibility that the impaired excretion of solute in kidney disease is due in part to diminished endogenous production of VEGF with consequent decrease in either the density or permeability of the renal capillary beds.

Essential hypertension, while not linked to renal disease per se, is associated with decreased renal natriuretic response to salt loading or increased intravascular volume or increased systemic blood pressure. Johnson and Schreiner (1997). Hypertension, as an expression of altered transport of sodium chloride across a basement membrane in the kidney, may be a consequence of diminished number or porosity of the capillary plexus subserving the sodium chloride transporting epithelia of the renal nephron.

It has now been shown that, using a model of hypertension dependent upon increased sodium in the diet, the administration of an angiogenic factor which increases the number and/or porosity of capillaries adjacent to the transporting epithelium allows increased solute load in the diet such that it can be handled in a non-hypertensive manner.

Without being bound by any one theory, a relative deficiency in VEGF could predispose to systemic hypertension several ways. First, the loss of constitutive VEGF expression at sites of tubulointerstitial damage may play a role in the capillary loss at these sites, since VEGF is a potent angiogenic factor. Second, the endothelium in the glomeruli and peritubular capillaries are relatively unique in that they express fenestrations. VEGF is the only cytokine known to induce endothelial fenestrations, and the constitutive sites of VEGF expression in the kidney (podocytes and collecting duct cells) suggests that they normally help maintain this endothelial phenotype. It is possible that the local loss of VEGF could reduce these fenestrations, and that this could impact on glomerular permeability (kf) or the relative permeability of the peritubular capillaries involved in pressure natriuresis (i.e., an "interstitial" ki). Finally, since VEGF is a potent inducer of eNOS expression and NO generation, a loss of VEGF could theoretically result in decreased local NO concentration.

Experiments set forth in the Examples, in which $VEGF_{121}$ was infused to rats with tubulointerstitial disease induced either by angiotension II (AII) or cyclosporine (CSA), demonstrated that VEGF infusion could prevent the development of salt-sensitive hypertension, and in the CSA model this was shown to persist even after VEGF administration was stopped.

An angiogenic factor, such as VEGF, may restore the proper response to salt loading by restoring trans-basement membrane transport of solutes such as sodium and chloride. Accordingly, the treatment of hypertension can now be mediated by increasing either the density of capillaries adjacent to the basement membrane, the porosity of the capillaries, or both.

There has been no previous attempt to stimulate sodium chloride excretion by the kidney by stimulating angiogenesis and/or porosity of the blood vessels, with consequent blood pressure normalization. No previous therapy has targeted the endothelium to improve the efficiency of solute transport. Indeed, it has heretofor been believed that administration of an angiogenic factor in this context would be detrimental. Unlike other therapies, it has now been found that angiogenic therapy further addresses the mechanism by which the kidney is impaired with respect to excreting increased salt loads.

Accordingly, the methods of the present invention treat hypertension by administering an amount of angiogenic factors effective to decrease hypertension. Such factors may stimulate angiogenesis and/or promote vascular permeability.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

Definitions

The term "angiogenic factor", as used herein, refers to any molecule (including polypeptides, peptides and small molecules), capable of promoting the growth of new blood capillary vessels from existing endothelium (angiogenesis), and/or increasing vascular permeability (promoting porosity of blood vessels. Angiogenic factors include, but are not limited to, vascular endothelial growth factors (VEGFs) in all forms, including native sequence VEGF molecules from any animal species, including humans, and their functional derivatives, fibroblast growth factors (FGFs), such as acidic and basic fibroblast growth factors (aFGFs and bFGFs) in all forms, including native sequence FGF molecules from any animal species, including humans, and their functional derivatives, and VEGF-related molecules, such as PlGF, VEGF-B, and VEGF-C/VRP, including all native sequence forms from any animal species, including humans and other mammalian species, such as murine, bovine, equine, porcine, ovine, canine, or feline, and their functional derivatives. The definition specifically includes homo- and heterodimeric forms of these and related molecules, where dimerization is required for biological activity.

Such factors include VEGF, in any of its forms, and other angiogenic factors, including, but not limited to, basic fibroblast growth factor and acidic fibroblast growth factor. Additionally, such factors include those that stimulate the production of VEGF or other angiogenic factors or the expression of VEGF receptors or the receptors of other angiogenic factors. Such factors include, but are not limited to, platelet derived growth factor (PDGF), transforming growth factor (TGF-α or -β), interleukin-1 (IL-1), interleukin-6 (IL-6), insulin-like growth factor (FGF) in all its forms, heparin-binding epidermal growth factor (HBEGF), epidermal growth factor (EGF), adenosine, prostaglandins (PGs), and agents that activate protein kinase C, protein kinase A, or ras GTPase activating proteins.

Additions, substitutions or deletions of portions of any angiogenic factor are acceptable as long as the modification allows the factor to retain biological activity. Representative measures of biological activity are known in the art and include, but are not limited to, including initiation or promotion of angiogenesis in vivo, and/or promotion of blood vessel porosity in vivo, or stimulation of endothelial mitosis or chemotaxis, or nitric oxide production in vitro or in vivo, or promotion of the formation and secretion of factors that exert the aforementioned effects. Preferably, a "biologically active angiogenic factor" is one that increases angiogenesis and/or increases vascular/capillary permeability. An angiogenic factor can be part of a fusion polypeptide, i.e., one that comprises a portion that is the angiogenic factor and at least one other portion that comprises a different polypeptide. Examples include epitope-tagged angiogenic factors. Covalent modifications, which are known in the art, are also possible and included for use herein. A particularly professed biological activity for the purpose of this invention is the ability to reduce, most preferably, normalize hypertension.

The phrase "factor that stimulates the production of an angiogenic factor", and grammatical equivalents thereof, are used in the broadest sense, and include compounds (native and variant polypeptides and peptides, small molecules, antibodies, etc.) that stimulate the expression of angiogenic factors, or receptors of angiogenic factors, regardless of the mechanism by which this stimulation is achieved. As noted before, such factors include, for example, platelet derived growth factors (PDGF) in all forms, transforming growth factors (TGF) in all forms, interleukin-1 (IL-1), interleukin-6 (IL-6), insulin-like growth factor (IGF) in all forms, heparin-binding epidermal growth factor, epidermal growth factor (EGF), adenosine, prostaglandins, or agents that activate protein kinase C, protein kinase A, or ras GTPase activating proteins. The designations of the listed angiogenic factors specifically include all naturally occurring forms from any animal species, including humans and other mammalian species, such as murine, bovine, equine, porcine, ovine, canine, or feline, and functional derivatives thereof.

The term "vascular endothelial growth factor" or "VEGF" as used herein refers to any naturally occurring (native) forms of a VEGF polypeptide (also known as "vascular permeability factor" or "VPF") from any animal species, including humans and other mammalian species, such as murine, bovine, equine, porcine, ovine, canine, or feline, and functional derivatives thereof. "Native human VEGF" consists of two polypeptide chains generally occurring as homodimers. Each monomer occurs as one of five known isoforms, consisting of 121, 145, 165, 189, and 206 amino acid residues in length. These isoforms will be hereinafter referred to as $hVEGF_{121}$, $hVEGF_{145}$, $hVEGF_{165}$, $hVEGF_{189}$, and $hVEGF_{206}$, respectively. Similarly to the human VEGF, "native murine VEGF" and "native bovine VEGF" are also known to exist in several isoforms, 120, 164, and 188 amino acids in length, usually occurring as homodimers. With the exception of $hVEGF_{121}$, all native human VEGF polypeptides are basic, heparin-binding molecules. hVEGF$_{121}$ is a weakly acidic polypeptide that does not bind to heparin. These and similar native forms, whether known or hereinafter discovered are all included in the definition of "native VEGF" or "native sequence VEGF", regardless of their mode a preparation, whether isolated from nature, synthesized, produced by methods of recombinant DNA technology, or any combination of these and other techniques. The term "vascular endothelial growth factor" or "VEGF" includes VEGF polypeptides in monomeric, homodimeric and heterodimeric forms. The definition of "VEGF" also includes a 110 amino acids long human VEGF species (hVEGF$_{110}$), and its homologues in other mammalian species, such as murine, bovine, equine, porcine, ovine, canine, or feline, and functional derivatives thereof. In addition, the term "VEGF" covers chimeric, dimeric proteins, in which a portion of the primary amino acid structure corresponds to a portion of either the A-chain subunit or the B-chain subunit of platelet-derived growth factor, add a portion of the primary amino acid structure corresponds to a portion of vascular endothelial growth factor. In a particular embodiment, a chimeric molecule is provided consisting of one chain comprising at least a portion of the A- or B-chain subunit of a platelet-derived growth factor, disulfide linked to a second chain comprising at least a portion of a VEGF molecule. More details of such dimers are provided, for example, in U.S. Pat. Nos. 5,194,596 and 5,219,739 and in European Patent EP-B 0 484 401, the disclosures of which are hereby expressly incorporated by reference. The nucleotide and amino acid sequences of hVEGF$_{121}$ and bovine VEGF$_{120}$ are disclosed, for example, in U.S. Pat. Nos. 5,194,596 and 5,219,739, and in EP 0 484 401. hVEGF$_{145}$ is described in PCT Publication No. WO 98/10071; hVEGF$_{165}$ is described in U.S. Pat. No. 5,332,671; hVEGF$_{189}$ is described in U.S. Pat. No. 5,240,848; and hVEGF$_{206}$ is described in Houck et al. *Mol. Endocrinol.* 5:1806–1814 (1991). Other VEGF polypeptides and polynucleotides have been described, including, for example, zvegf2 (PCT Publication No. WO 98/24811), and VRP (PCT Publication No. WO 97/09427), and are also encompassed by the term VEGF. For the disclosure of the nucleotide and amino acid sequences of various human VEGF isoforms see also Leung et al., *Science* 246:1306–1309 (1989); Keck et al., *Science* 246:1309–1312 (1989); Tisher et al., *J. Biol. Chem.* 266:11947–11954 (1991); EP 0 370 989; and PCT publication WO 98/10071. Forms of VEGF are shown schematically in FIG. 1. FIGS. 2–11 (SEQ ID NOs: 1–10) show the nucleotide and amino acid sequences of various VEGF species. For further review, see also Klagsburn and D'Amore, *Cytokine and Growth Factor Reviews* 7:259–170 (1996).

The term "VEGF" encompasses a polypeptide having an amino acid sequence substantially homologous to one or more of the above-mentioned native VEGF polypeptides, and which retains a biological activity associated with VEGF. An amino acid sequence is considered to be "substantially homologous" herein if the level of amino acid sequence homology is at least about 50%, preferably at least about 80%, more preferably at least about 90%, most preferably, at least about 95%, compared with the native VEGF protein in question.

Also included within the scope of "VEGF" herein are biologically active fragments thereof, as well as N-terminally or C-terminally extended versions thereof or analogs thereof substituting and/or deleting or inserting one or more amino acid residues which retain qualitatively the biological activities of the protein described herein. Preferred analogs include those in which one or more cysteine residues not required for biological activity are substituted by a different amino acid residue, preferably serine. Substitution of one or more cysteine residues reduces the opportunity for intermolecular and intramolecular disulfide bond formation, thereby rendering the molecule more stable. For example, there are nine cysteine residues that are present in hVEGF 121 and hVEGF165. Of these, eight are conserved with PDGF. Accordingly, a preferred analog is one in which the ninth cysteine residue is substituted by serine. This cysteine residue is present at position 160 of hVEGF 165 and position 116 of hVEGF 121. Amino acid substitutions can be accomplished by site specific mutagenesis of the DNA sequences described herein using well known techniques. See, e.g., Zoller and Smith (1982) *Nucleic Acids Research* 10:6487–6500.

The term "VEGF" specifically includes homodimeric and heterodimeric forms of the VEGF molecule, in which the dimer is formed via interchain disulfide bonds between two subunits. Homodimers may have both of their subunits unglycosylated or glycosylated, while in heterodimers, one subunit may be glycosylated and the other unglycosylated. The term "VEGF" specifically includes not only amino acid sequence variants but also glycosylation variants of the native VEGF molecules.

In addition, the term "VEGF" covers chimeric, dimeric proteins, in which a portion of the primary amino acid structure corresponds to a portion of either the A-chain subunit or the B-chain subunit of platelet-derived growth factor, add a portion of the primary amino acid structure corresponds to a portion of vascular endothelial growth factor. In a particular embodiment, a chimeric molecule is provided consisting of one chain comprising at least a portion of the A- or B-chain subunit of a platelet-derived growth factor, disulfide linked to a second chain comprising at least a portion of a VEGF molecule. More details of such dimers are provided, for example, in U.S. Pat. Nos. 5,194,596 and 5,219,739 and in European Patent EP-B 0 484 401, the disclosures of which are hereby expressly incorporated by reference.

The amino acid sequence numbering system used herein for VEGF is based on the mature forms of the protein, i.e. the post-translationally processed forms. Accordingly, the residue numbered one in the human proteins is alanine, which is the first residue of the isolated, mature forms of these proteins.

A "polynucleotide comprising sequences encoding an angiogenic factor" includes a polynucleotide comprising sequences encoding any of the above-mentioned angiogenic factors. Many such polynucleotides have been disclosed, including, for example, in the references mentioned above, wherein VEGF polypeptides are disclosed. The term encompasses polynucleotide sequences which hybridize under stringent hybridization conditions to the disclosed sequences, as long as the polypeptide encoded thereby is biologically active, i.e., it increases angiogenesis and/or increases vascular permeability.

The terms "vector", "polynucleotide vector", "construct" and "polynucleotide construct" are used interchangeably herein. A polynucleotide vector of this invention may be in any of several forms, including, but not limited to, RNA, DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, complexed with compounds such as PEG to immunologically "mask" the molecule and/or increase half-life, or conjugated to a non-viral protein. A polynucleotide vector of this invention may be in the form of any of the delivery vehicles described herein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

"Under transcriptional control" is a term well-understood in the art and indicates that transcription of a polynucleotide sequence, usually a DNA sequence, depends on its being operably (operatively) linked to an element which contributes to the unification of, or promotes transcription.

A "host cell" includes an individual cell or cell culture which can be or has been a recipient of any vector of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo with a vector comprising a polynucleotide encoding an angiogenic factor.

An "individual" is a vertebrate, preferably a mammal, more preferably a human. Mammals include, but are not limited to, farm animals, sport animals, and pets.

An "effective amount" is an amount sufficient to effect beneficial or desired clinical results. An effective amount can be administered in one or more administrations. For purposes of this invention, an effective amount of an angiogenic factor is an amount that is sufficient to palliate, ameliorate, stabilize, reverse, slow or delay the progression of the disease state. In particular, the "effective amount" for the purpose of the present invention is defined as an amount capable of reducing, and preferably normalizing, at least transiently, high blood pressure in an accepted animal model of hypertension, such as, for example, the animal model of salt-dependent hypertension disclosed in Example 2 herein.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. Accordingly, "treatment" in the context of the present invention is an intervention performed with the intention of preventing the development of high blood pressure in patients at risk and/or or reducing elevated blood pressure, preferably to a normal level. For maintenance of acceptable levels of blood pressure, repeated treatments may be necessary for an extended period of time.

"Palliating" a disease means that the extent and/or undesirable clinical manifestations of a disease state are lessened and/or time course of the progression is slowed or lengthened, as compared to not administering a factor which increases angiogenesis and/or vascular permeability.

Effectiveness is determined by decreased blood pressure in response to salt loading. Methods of measuring blood pressure are known in the art and need not be described herein.

"Sequence identity", is defined as the percentage of amino acid residues in a candidate sequence that are identical with the amino acid residues in a native polypeptide sequence, after aligning the sequences and introducing gaps, if necessary, to achieve the maximum percent sequence identity, and not considering any conservative substitutions as part of the sequence identity. The % sequence identity values are generated by the NCBI BLAST2.0 software as defined by Altschul et al., (1997), "Gapped BLAST and PSI-BLAST: a new generation of protein database search programs", *Nucleic Acids Res.*, 25:3389–3402. The parameters are set to default values, with the exception of the Penalty for mismatch, which is set to −1.

"Mammal" for purposes of treatment refers to any animal classified as a mammal, including humans, domestic and farm animals, and zoo, sports, or pet animals, such as horses, sheep, cows, pigs, dogs, cats, etc. Preferably, the mammal is human.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

Administration "in combination with" one or more further therapeutic agents includes simultaneous (concurrent) and consecutive administration in any order.

The term "agonist" is used in the broadest sense and includes any molecule that mimics a biological activity of a native angiogenic factor, such as a native VEGF polypeptide disclosed herein. For the purpose of the methods claimed herein, the biological activity mimicked is the ability to reduce elevated blood pressure, regardless of the mechanism by which this effect is achieved. Suitable molecules specifically include agonist or antagonist antibodies or antibody fragments, fragments or amino acid sequence variants of native polypeptides, peptides, small organic molecules, etc.

A "small molecule" is defined herein to have a molecular weight below about 500 daltons.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases formino part of, the β-sheet structure. The CDRs in each chain are held together in close proximity by the FR regions and, with the CDRs from the other chain, contribute to the formation of the antigen-binding site of antibodies (see Kabat et al., *NIH Publ. No.* 91-3242, Vol. I, pages 647–669 (1991)). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" to "CDR" (i.e. residues 24–34 (L1), 50–56 (L2) and 89–97 (L3) in the light chain variable domain and 31–35 (H1), 50–65 (H2) and 95–102 (H3) in the heavy chain variable domain; Kabat et al., *Sequences of Proteins of Immunological Interest*, 5th Ed. Public Health Service, National Institute of Health, Bethesda, Md. [1991]) and/or those residues from a "hypervariable loop" (i.e. residues 26–32 (L1), 50–52 (L2) and 91–96 (L3) in the light chain variable domain and 26–32 (H1), 53–55 (H2) and 96–101 (H3) in the heavy chain variable domain; Clothia and Lesk, *J. Mol. Biol.* 196:901–917 [1987]). "Framework" or "FR" residues are those variable domain residues other than the hypervariable region residues as herein defined.

The term "antibody" is used herein in the broadest sense and specifically covers, without limitation, intact monoclonal antibodies, polyclonal antibodies, multispecific antibodies (e.g. bispecific antibodies) formed from at least two intact antibodies, and antibody fragments so long as they exhibit the desired biological activity.

"Antibody fragments" comprise a portion of an intact antibody, preferably the antigen binding or variable region of the intact antibody. Examples of antibody fragments include, for example, Fab, Fab', F(ab')$_2$, and Fv fragments; diabodies; linear antibodies (Zapata et al., *Protein Eng.* 8(10):1057–1062 [1995]); single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 [1975], or may be made by recombinant DNA methods (see, e.g., U.S. Pat. No. 4,816,567). The "monoclonal antibodies" may also be isolated from phage antibody libraries using the techniques described in Clackson et al., *Nature*, 352:624–628 [1991] and Marks et al., *J. Mot. Biol.*, 222:581–597 (1991), for example.

The monoclonal antibodies herein specifically include "chimeric" antibodies in which the variable region of an antibody heavy or light chain is derived from one mammalian species (typically a rodent, e.g. mouse, rat or rabbit), while the constant region is derived from a different mammalian species (typically human), as well as fragments of such antibodies, so long as they exhibit the desired biological activity (U.S. Pat. No. 4,816,567; Morrison et al., *Proc. Natl. Acad. Sci. USA*, 81:6851–6855 [1984]).

"Humanized" forms of non-human (e.g., murine) contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat or rabbit having the desired specificity, affinity, and capacity. In some instances, Fv FR residues of the human immunoglobulin are replaced by corresponding non-human residues. Furthermore, humanized antibodies may comprise residues which are found neither in the recipient antibody nor in the imported CDR or framework sequences. The humanized antibody optimally also will comprise at least a portion of an immunoglobulin constant region (Fc), typically that of a human immunoglobulin. For further details, see Jones et al., *Nature*, 321:522–525 (1986); and Reichmann et al., *Nature*, 332:323–329 [1988]. The humanized antibody includes a PRIMATIZED™ antibody wherein the antigen-binding region of the antibody is derived from an antibody produced by immunizing macaque monkeys with the antigen of interest.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenburg and Moore eds., Springer-Verlag, New York, pp. 269–315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$–$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444–6448 (1993).

Angiogenic Factors

The present invention provides methods for treating hypertension comprising administering an effective amount of an angiogenic factor. An angiogenic factor suitable for use in the methods of the present invention can promote (or increase, or induce) angiogenesis and/or can promote (or increase, or induce) vascular or capillary permeability. An angiogenic factor can be used singly or in combination with another angiogenic factor(s) or other therapeutic agents for use in the methods described herein.

An angiogenic factor can be a biological or chemical compound such as a simple or complex organic or inorganic molecule, a peptide, or a protein. A vast array of compounds can be synthesized, for example, oligopeptides, and synthetic inorganic and organic compounds based on various core structures, and these are also included.

Whether an angiogenic factor promotes angiogenesis can be determined by any known method. For example, a material which serves as a matrix for invasion of new blood vessels, such as, for example, gelatin or Matrigel, can be implanted subcutaneously in an animal. The implanted sponges can be treated with a putatitive angiogenic factor and, after a suitable period of time, e.g., 7 to 14 days, the implants are removed and examined morphometrically for the quantitation of blood vessels which have invaded the implant. Alternatively, the implants can be analyzed for the presence of an endothelial cell marker, such as von Willebrand factor or CD34, or the hemoglobin content of the implant can be determined. Vascularization of an implant containing a putative angiogenic factor is compared with an implant lacking the factor. In vitro methods for assessing angiogenesis have also been described and can be used to determine whether a substance is an angiogenic factor. Magee et al. (1994) *Am. J. Physiol.* 267:pL433–441; Pepper et al. (1992) *Biochem. Biophys. Res. Comm.* 189:824–831; and Nicosia et al. (1994) *Am. J. Pathol.* 145:1023–1029.

produced by any known means, including those described in U.S. Pat. No. 5,194,596.

Amino Acid Sequence Variants of Native Angiogenic Factors

Variations in the amino acid sequence of native angiogenic factors, such as native VEGF polypeptides, involve substitution, deletion and/or insertion of one or more amino acids in the native polypeptide sequence. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in any assay of high blood pressure, such as the assay described in the Examples below.

In a preferred group of amino acid sequence variants, one ore more cysteine residues in the VEGF structure is replaced by another amino acid. Such substitution reduced the opportunity for intermolecular and intramolecular disulfide bond formation, thereby rendering the molecule more stable. There are nine cysteine residues present in hVEGF120, hVEGF165, and in the respective bovine homologues. Of these, eight are conserved with PDGF. Accordingly, the most preferred analog is in which the ninth cysteine residue is subtituted by serine. This cysteine residue is presented at position 160 of hVEGF165 and position 116 of hVEGF121, and the corresponding positions of the bovine forms. Some additional information about variant forms of VEGF molecules is provided in U.S. Pat. No. 5,332,671. Specifically included herein are the variant VEGF molecules described in PCT Publication WO 98/36075, the disclosure of which is expressly incorporated by reference. Such VEGF molecules contain modifications in the C-terminal heparin binding domain that are described to result in functional modification of the pharmacokinetic profile, and yield molecules having a reduced clearance rate compared with the corresponding heparin-binding native VEGF molecule. Preferred embodiments include the replacement of positively charged amino acids with negatively charged or neutral amino acids within the heparin-binding domain of a heparin-binding VEGF species. In addition, VEGF variants in which portions of the C-terminal heparin-binding domain are deleted are included within the scope of the present invention.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other Inown techniques can be performed on the cloned DNA to produce the DNA encoding a VEGF variant.

Scanning amino acid analysis can also be employed to identify one or more amino acids along a contiguous sequence. Among the preferred scanning amino acids are relatively One indication that a factor promotes angiogenesis is its ability to induce mitogenesis of vascular endothelial cells. Mitogenic activity for vascular endothelial cells can be determined by an assay which uses, as target cells, adrenal cortex-derived capillary endothelial cells (ACE cells). This assay is carried out essentially as described in Gospodarowicz et al. ((1986) *J. Cell Physiol.* 127:121–136), the disclosure of which is incorporated herein by reference. Generally, stock cultures of ACE cells are maintained in the presence of Dulbeeco's modified Eagle's medium (DMEM-21) supplemented with 10% calf serum. The antibiotics penicillin (50 IU/ml), streptomycin (50 mu g/ml), gentamycin (50 mu g/ml), and Fungizone (0.25 mu g/ml) and 2 mM L-glutamine can also be added to the medium. Cells are passaged weekly on tissue culture dishes at a split ratio of between 1:40 and 1:200 (the preferred split ratio is that which gives $2.5 \times 10^5$ cells in 15 ml of medium in T75 flasks). For the mitogenic assay, cells are seeded in 12 well cluster plates at a density of $5 \times 10^3$ cells per well in 1 ml Dulbecco's modified Eagle's medium supplemented with 10% calf serum and antibiotics as described in Gospodarowicz et al. (1988) *Eur. J. Cell. Biol.* 46:144–151. Alternatively, the ACE cells are plated in 35 mm dishes or 6 well cluster plates at a density of $5-10 \times 10^3$ cells per dish or well in 2 ml of medium as described in Gospodarowicz et al. (1986). Ten-microliter aliquots of appropriate dilutions of each sample are then added to duplicate or triplicate wells in the dishes on days 0 and 2. After 4 or 5 days in culture, the plates are trypsinized and cell densities determined in a Coulter counter. For purposes of description herein, a factor is considered to have mitogenic activity for vascular endothelial cells if the cell density at the end of this assay is at least 1.5 times and preferably at least 3 times the cell density of control wells receiving no factor additions.

Determination of whether an angiogenic factor induces capillary permeability can be determined by any known method. The method used may depend upon the tissue being examined. For example, for determination of renal peritubular capillary permeability, one can administer to an animal proteins of various molecular weights which are labelled with a dye detectable by electron microscopy. Venkatachalam and Karnovsky (1972) *J. Lab. Invest.* 27:435–444. Alternatively, the proteins can be enzymes which act on a substrate to produce a signal. Another method to measure peritubular capillary permeability is by renal micropuncture. See, for example, Baer et al. (1978) *Kidney Int.* 13:452–466. Methods to assess capillary permeability in the lung have been described (Lull et al. (1983) *Semin. Nucl. Med.* 13:223–237), as have methods to measure cerebral vascular permeability (Terada et al. (1992) *Neuroradiol.* 34:290–296).

Capillary density can be measured immunohistochemically using commercially available antibodies which bind specifically to endothelial cell-specific cell surface markers, such as von Willebrand factor or CD34.

In determining whether an angiogenic factor is effective in treating hypertension, an animal model such as the one described herein can be used. Hypertension is induced, as described in Example 1, a putative angiogenic factor administered, and blood pressure monitored. Decreased blood pressure in response to treatment with the factor, as compared with a hypertensive animal not treated with the factor, is an indication that the factor is effective in treating hypertension. Other animal models of hypertension are known in the art, and can be used to determine whether an angiogenic factor is effective in treating hypertension. These include the Dahl rat. Roman et al. (1986) *Am. J. Physiol.* 251:F57–F65.

Production of Angiogenic Factors

Methods of producing known angiogenic factors are well known in the art and can be used to produce an angiogenic factor. These methods include synthetic and recombinant methods, as well as methods for isolating angiogenic factors from natural sources, from tissue culture supernatants, and the like. An example of an angiogenic factor which can be used in the methods of the present invention is VEGF, which can be small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244: 1081–1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

Delivery Vehicles Comprising Polynucleotides Encoding an Angiogenic Factor

The present invention also provides delivery vehicles suitable for delivery of a polynucleotide encoding an angiogenic factor into cells (whether in vivo, ex vivo, or in vitro). Generally, a polynucleotide encoding an angiogenic factor will be operably linked to a promoter and a heterologous polynucleotide. A polynucleotide encoding an angiogenic factor can be contained within a cloning or expression vector, using methods well known in the art, or within a viral vector. These vectors (especially expression vectors) can in turn be manipulated to assume any of a number of forms which may, for example, facilitate delivery to and/or entry into a target cell. Delivery of the polynucleotide constructs of the invention to eukaryotic cells, particularly to mammalian cells, more particularly to distal tubule cells of the kidney, can be accomplished by any suitable art-known method. Delivery can be accomplished in vivo, ex vivo, or in vitro.

The invention provides methods and compositions for transferring such expression constructs into cells, especially in vivo for treatment of hypertension. It is also an object of the invention to provide compositions for the therapy of hypertension.

Delivery vehicles suitable for incorporation of a polynucleotide encoding an angiogenic factor of the present invention for introduction into a host cell include nonviral vehicles and viral vectors. Verma and Somia (1997) *Nature* 389:239–242.

A wide variety of non-viral vehicles for delivery of a polynucleotide encoding an angiogenic factor are known in the art and are encompassed in the present invention. A polynucleotide encoding an angiogenic factor can be delivered to a cell as naked DNA (U.S. Pat. No. 5,692,622; WO 97/40163). Alternatively, a polynucleotide encoding an angiogenic factor can be delivered to a cell associated in a variety of ways with a variety of substances (forms of delivery) including, but not limited to cationic lipids; biocompatible polymers, including natural polymers and synthetic polymers; lipoproteins; polypeptides; polysaccharides; lipopolysaccharides; artificial viral envelopes; metal particles; and bacteria. A delivery vehicle can be a microparticle. Mixtures or conjugates of these various substances can also be used as delivery vehicles. A polynucleotide encoding an angiogenic factor can be associated noncovalently or covalently with these various forms of delivery. Liposomes can be targeted to a particular cell type, e.g., to a glomerular epithelial cell.

Viral vectors include, but are not limited to, DNA viral vectors such as those based on adenoviruses, herpes simplex virus, poxviruses such as vaccinia virus, and parvoviruses, including adeno-associated virus; and RNA viral vectors, including, but not limited to, the retroviral vectors. Retroviral vectors include murine leukemia virus, and lentiviruses such as human immunodeficiency virus. Naldini et al. (1996) *Science* 272:263–267.

Non-viral delivery vehicles comprising a polynucleotide encoding an angiogenic factor can be introduced into host cells and/or target cells by any method known in the art, such as transfection by the calcium phosphate coprecipitation technique; electroporation; electropermeabilization; liposome-mediated transfection; ballistic transfection; biolistic processes including microparticle bombardment, jet injection, and needle and syringe injection; or by microinjection. Numerous methods of transfection are known to the skilled worker in the field.

Viral delivery vehicles can be introduced into cells by infection. Alternatively, viral vehicles can be incorporated into any of the non-viral delivery vehicles described above for delivery into cells. For example, viral vectors can be mixed with cationic lipids (Hodgson and Solaiman (1996) *Nature Biotechnol.* 14:339–342); or lamellar liposomes (Wilson et al. (1977) *Proc. Natl. Acad. Sci. USA* 74:3471; and Faller et al. (1984) *J. Virol.* 49:269).

For in vivo delivery, the delivery vehicle(s) can be introduced into an individual by any of a number of methods, each of which is familiar in the art.

Pharmaceutical Compositions

Pharmaceutical compositions for use in the methods of the present invention can comprise a polynucleotide encoding an angiogenic, or, alternatively, pharmaceutical compositions can comprise an angiogenic factor itself.

Suitable forms, in part, depend upon the use or the route of entry, for example oral, transdermal, or by injection. Such forms should allow the agent or composition to reach a target cell whether the target cell is present in a multicellular host or in culture. For example, pharmacological agents or compositions injected into the blood stream should be soluble. Other factors are known in the art, and include considerations such as toxicity and forms which prevent the agent or composition from exerting its effect.

Compositions comprising an angiogenic factor or an angiogenic factor-encoding polynucleotide can also be formulated as pharmaceutically acceptable salts (e.g., acid addition salts) and/or complexes thereof. Pharmaceutically acceptable salts are non-toxic at the concentration at which they are administered.

Pharmaceutically acceptable salts include acid addition salts such as those containing sulfate, hydrochloride, phosphate, sulfonate, sulfamate, sulfate, acetate, citrate, lactate, tartrate, methanesulfonate, ethanesulfonate, benzenesulfonate, p-toluenesulfonate, cyclolexylsulfonate, cyclohexylsulfamate and quinate. Pharmaceutically acceptable salts can be obtained from acids such as hydrochloric acid, sulfuric acid, phosphoric acid, sulfonic acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including, but not limited to, intravenous, intraperitoneal, subcutaneous, and intramuscular, oral, topical, or transmucosal.

The desired isotonicity of the compositions can be accomplished using sodium chloride or other pharmaceutically acceptable agents such as dextrose, boric acid, sodium tartrate, propylene glycol, polyols (such as mannitol and sorbitol), or other inorganic or organic solutes.

Pharmaceutical compositions comprising an angiogenic factor or a polynucleotide encoding an angiogenic factor can be formulated for a variety of modes of administration, including systemic and topical or localized administration. Techniques and formulations generally may be found in *Remington's Pharmaceutical Sciences*, 18th Edition, Mack Publishing Co., Easton, Pa. 1990. See, also, Wang and Hanson *"Parenteral Formulations of Proteins and Peptides: Stability and Stabilizers", Journal of Parenteral Science and Technology*, Technical Report No. 10, Supp. 42-2S (1988). A suitable administration format can best be determined by a medical practitioner for each patient individually.

For systemic administration, injection is preferred, e.g., intramuscular, intravenous, intraperitoneal, subcutaneous, intrathecal, or intracerebrovascular. For injection, the compounds of the invention are formulated in liquid solutions, preferably in physiologically compatible buffers such as Hank's solution or Ringer's solution. Alternatively, the compounds of the invention are formulated in one or more excipients (e.g., propylene glycol) that are generally accepted as safe as defined by USP standards. They can, for example, be suspended in an inert oil, suitably a vegetable oil such as sesame, peanut, olive oil, or other acceptable carrier. Preferably, they are suspended in an aqueous carrier, for example, in an isotonic buffer solution at pH of about 5.6 to 7.4. These compositions can be sterilized by conventional sterilization techniques, or can be sterile filtered. The compositions can contain pharmaceutically acceptable auxiliary substances as required to approximate physiological conditions, such as pH buffering agents. Useful buffers include for example, sodium acetate/acetic acid buffers. A form of repository or "depot" slow release preparation can be used so that therapeutically effective amounts of the preparation are delivered into the bloodstream over many hours or days following transdermal injection or delivery. In addition, the compounds can be formulated in solid form and redissolved or suspended immediately prior to use. Lyophilized forms are also included.

Alternatively, the compounds can be administered orally. For oral administration, the compounds are formulated into conventional oral dosage forms such as capsules, tablets and tonics.

Systemic administration can also be transmucosal or transdermal means, or the molecules can be administered orally. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents can be used to facilitate permeation. Transmucosal administration can be, for example, through nasal sprays or using suppositories. For oral administration, the molecules are formulated into conventional oral administration dosage forms such as capsules, tablets, and liquid preparations.

For topical administration, the compounds of the invention are formulated into ointments, salves, gels, or creams, as is generally known in the art.

If desired, solutions of the above compositions can be thickened with a thickening agent such as methyl cellulose. They can be prepared in emulsified form, either water in oil or oil in water. Any of a wide variety of pharmaceutically acceptable emulsifying agents can be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components can be mixed simply in a blender or other standard device to produce a concentrated mixture which can then be adjusted to the final concentration and viscosity by the addition of water or thickening agent and possibly a buffer to control pH or an additional solute to control tonicity.

The amounts of various compounds for use in the methods of the invention to be administered can be determined by standard procedures. Generally, a therapeutically effective amount is between about 1 nmole and 3 $\mu$mole of the molecule, preferably between about 10 nmole and 1 $\mu$mole depending on the age and size of the patient, and the disease or disorder associated with the patient. Generally, it is an amount between about 0.05 and 50 mg/kg, preferably 1 and 20 mg/kg of the individual to be treated.

For use by the physician, the compositions are provided in dosage unit form containing an amount of an angiogenic factor.

Antibodies

Some drug candidates according to the present invention are agonist antibodies which mimic the anti-hypertensive properties of an angiogenic factor, preferably a VEGF.

Methods of preparing polyclonal antibodies are known in the art. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. It may be useful to conjugate the immunizing agent to a protein known to be immunogenic in the mammal being immunized, such as serum albumin, or soybean trypsin inhibitor. Examples of adjuvants which may be employed include Freund's complete adjuvant and MPL-TDM.

According to one approach, monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. Preferred immortalized cell lines are those that fuse efficiently, support stable high level expression of antibody by the selected antibody-producing cells, and are sensitive to a medium such as HAT medium.

The culture medium in which the hybridoma cells are cultured can then be assayed for the presence of monoclonal antibodies directed against the particular angiogenic factor used, such as VEGF. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxy-lapatite chromatography, gel electrophoresis, dialysis, or affinity chromatography.

Alternatively, monoclonal antibodies may be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells discussed above serve as a preferred source of such DNA. Once isolated, the DNA may be placed into expression vectors, which are then transfected into host cells such as COS cells, Chinese hamster ovary (CHO) cells, or myeloma cells that do not otherwise produce immunoglobulin protein, to obtain the synthesis of monoclonal antibodies in the recombinant host cells.

The antibodies, including antibody fragments, such as Fv, Fab, Fab', F(ab')$_2$ or other antigen-binding subsequences of antibodies, may be humanized. Humanized antibodies contain minimal sequence derived from a non-human immunoglobulin. More specifically, in humanized antibodies residues from a complementary determining region (CDR) of a human immunoglobulin (the recipient) are replaced by residues from a CDR of a non-human species (donor antibody) such as mouse, rat or rabbit having the desired specificity, affinity and capacity. In some instances, Fv framework residues of the human immunoglobulin are also replaced by corresponding non-human residues. Humanized antibodies may additionally comprise residues that are found neither in the recipient antibody nor in the imported CDR or framework sequences [Jones et al., *Nature*, 321:522–525 (1986); Riechmann et al., *Nature*, 332:323–329 (1988)].

Methods for humanizing non-human antibodies are well known in the art. Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent DRs or CDR sequences for the corresponding sequences of a human antibody.

In addition, human antibodies can be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

The antibodies may be bispecific, in which one specificity is for an angiogenic factor, and the other specificity for another protein, such as, a second angiogenic factor, or a different epitope of the same angiogenic factor.

Screening Assays for Drug Candidates

Screening assays for drug candidates are designed to identify agonists, such as small molecule agonists, of the angiogenic factors (e.g. VEGF) used in the methods and compositions of the present invention. Such screening assays will include assays amenable to high-throughput screening of chemical libraries, making them particularly suitable for identifying small molecule drug candidates. Small molecules contemplated include synthetic organic or inorganic compounds, including peptides, preferably soluble peptides, (poly)peptide-immunoglobulin fusions, and antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. The assays can be performed in a variety of formats, including protein-protein binding assays, biochemical screening assays, immunoassays and cell based assays, which are well characterized in the art.

In addition, drug candidates can be tested or their initial activity can be confirmed in various animal models of hypertension (e.g. salt-sensitive hypertension). Microvascular injury has been identified as a possible mechanism for tubuinterstitial (TI) injury and associated salt-dependent hypertension. For example, it has been reported that short term infusion of angiotensin II (AII) results in focal TI injury, and predisposes rats to the subsequent development of salt-sensitive hypertension (Lombardi et al., *Hypertension* 33:1013–1019,1999). Similarly, aging has been strongly associated with salt-sensitive hypertension (Weinberger and Fineberg, *Hypertension* 18:67–71, 1991), and it was shown that tubulointerstitial damage in the aging rat is also susceptible to salt-sensitive hypertension (Masilamani et al., *Am. J. Kid. Des.* 32:605–610. 1998).

Methods of Treatment using an Angiogenic Factor

The invention provides methods for treating hypertension. The methods generally involve administering to an individual an amount of an angiogenic factor effective to decrease hypertension. An effective amount is as described above. Effectiveness of the treatment is determined by decreased blood pressure particularly in response to salt loading.

The methods of the present invention can also be useful in treating disorders relating to abnormal transport of solutes across endothelial cells. Such disorders include (1) the treatment or prevention of kidney disease associated with impaired filtration or excretion of solutes; (2) the treatment or prevention of diseases of the central nervous system associated with alterations in cerebrospinal fluid synthesis, composition, or circulation, including stroke, meningitis, tumor, infections, and disorders of bone growth; (3) the treatment or prevention of hypoxia or hypercapnia or fibrosis arising from accumulation of fluid secretions in the lungs or impediments to their removal, including but not restricted to acute respiratory distress syndrome, toxic alveolar injury, as occurs in smoke inhalation, pneumonia, including viral and bacterial infections, surgical intervention, cystic fibrosis, and other inherited or acquired disease of the lung associated with fluid accumulation in the pulmonary air space; (4) the treatment or prevention of pulmonary dysfunction arising from injury to the pulmonary endothelium, including disorders arising from birth prematurity, and primary and secondary causes of pulmonary hypertension; (5) the treatment or prevention of disease arising from disordered transport of fluid and solutes across the intestinal epithelium, including but not restricted to inflammatory bowel disease, infections diarrhea, surgical intervention; (6) the treatment or prevention of ascites accumulation in the peritoneum as occurs in failure of the heart, liver, or kidney, or in infectious or tumor states; (7) the enhancement of efficacy of solute flux as it can be needed for peritoneal dialysis in the treatment of kidney failure or installation of therapeutics or nutrition into the peritoneum; (8) the preservation or enhancement of function of organ allografts, including but not restricted to transplants of kidney, heart, liver, lung, pancreas, skin, bone, intestine, and xenografts; and (9) the treatment of cardiac valve disease.

The following examples are provided to illustrate but not limit the invention.

EXAMPLE 1

Plasma Elimination Kinetics of $VEGF_{121}$ and $VEGF_{165}$

Figure 2:
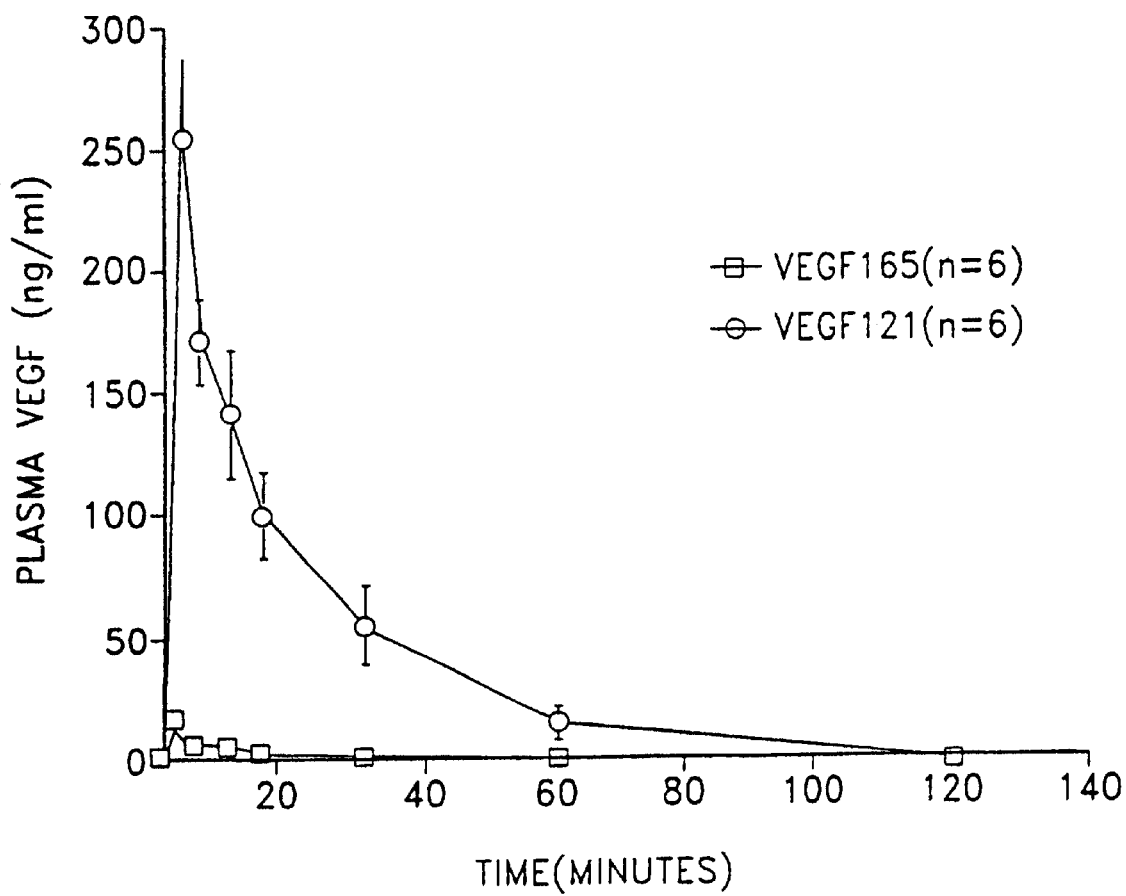
FIG. 2 is a graph depicting the plasma elimination kinetics of $VEGF_{121}$ and $VEGF_{165}$ administered intravenously. Each data point represents the average of the values obtained from six rats.
Figure 3:
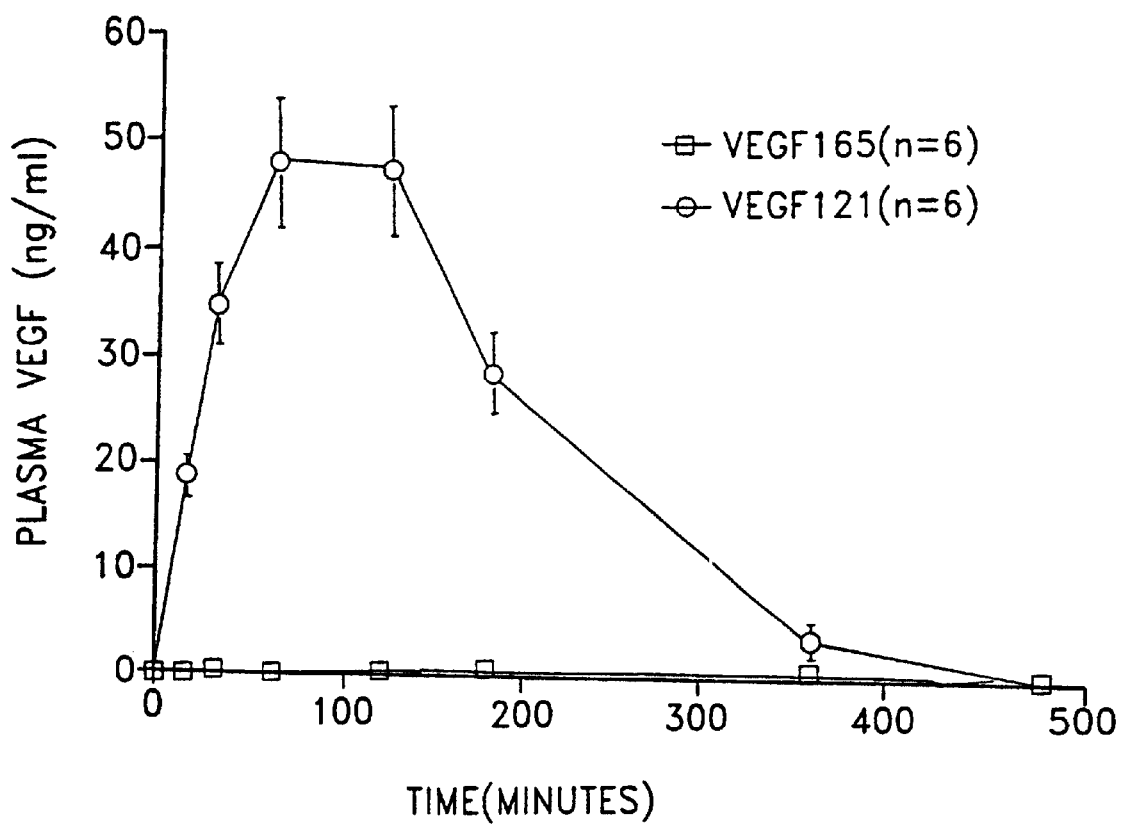
FIG. 3 is a graph depicting the plasma elimination kinetics of $VEGF_{121}$ and $VEGF_{165}$ administered subcutaneously. Each data point represents the average of the values obtained from six rats.

Studies were conducted to determine plasma elimination kinetics of $VEGF_{121}$ or $VEGF_{165}$ when administered intravenously or subcutaneously. Recombinant $VEGF_{121}$ or $VEGF_{165}$ was injected as a 10 μg/kg bolus into the tail veins of rats. Plasma samples were taken over the following two hours, and the concentration of VEGF in the samples was determined using a sandwich ELISA assay. The results are shown in FIG. 2. Recombinant $VEGF_{121}$ or $VEGF_{165}$ was injected into rats as a subcutaneous 100 μg/kg bolus. Plasma samples were taken over the following eight hours, and the concentration of VEGF in the samples was determined as before. The results are shown in FIG. 3. These data indicate that $VEGF_{121}$ exhibits the characteristics of being rapidly absorbed into the circulation following subcutaneous injection, remaining in circulation for a significant time period, and then being eliminated.

EXAMPLE 2

Animal Model of Salt-dependent Hypertension

Laboratory rats (e.g., Sprague-Dawley) can be rendered hypertensive in a salt-dependent manner to emulate the human example of essential hypertension. Indeed, recently published data (Lombardi et al., *Hypertension* 33:1013–1019, 1999) confirm that short term infusion of angiotension II (AII) results in focal tubulointerstitial (TI) injury and predisposes rats to the subsequent development of salt-sensitive hypertension.

Figure 4A:
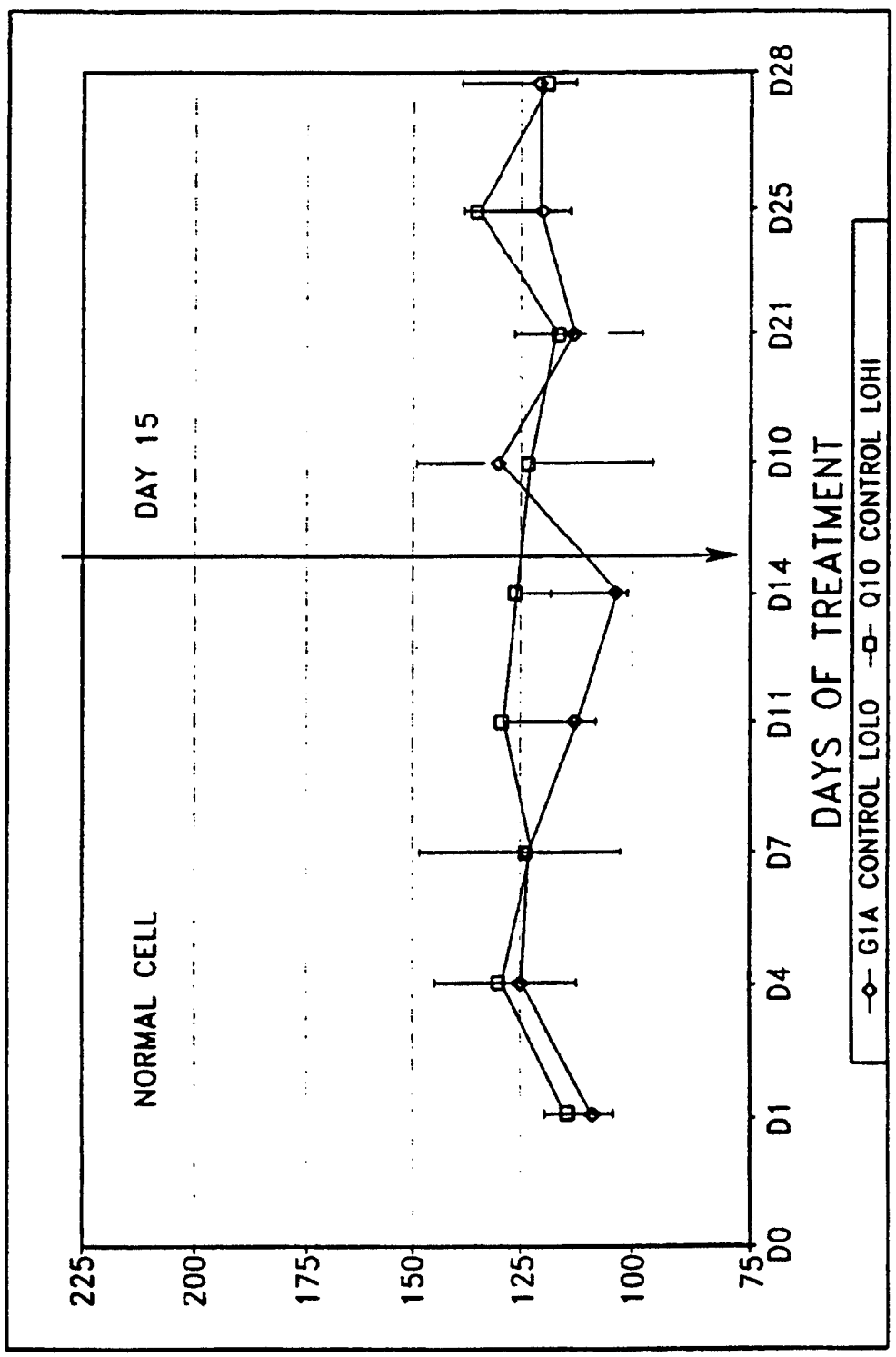
FIGS. 4a–c are graphs of systolic blood pressure versus days of treatment.

The model used in the present experiment consists of placing normal laboratory rats on a diet with an increased amount of sodium chloride (4% w/w) for three days. Rats were placed on this diet alone for up to two weeks. These rats showed no hypertension compared to rats on a normal lab chow diet, which comprises 0.1% NaCl (FIG. 4a).

Figure 4B:
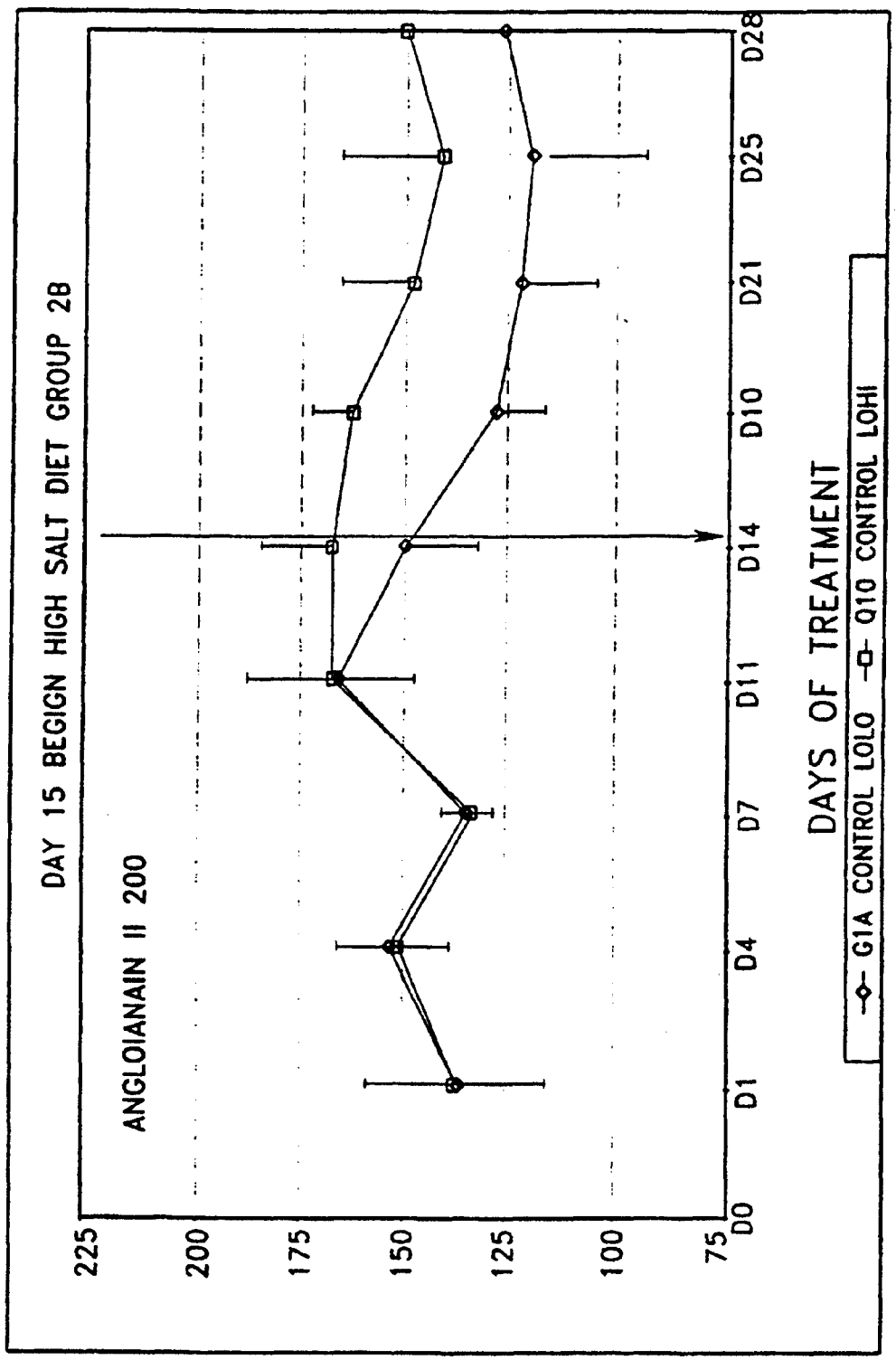
Figure 4C:
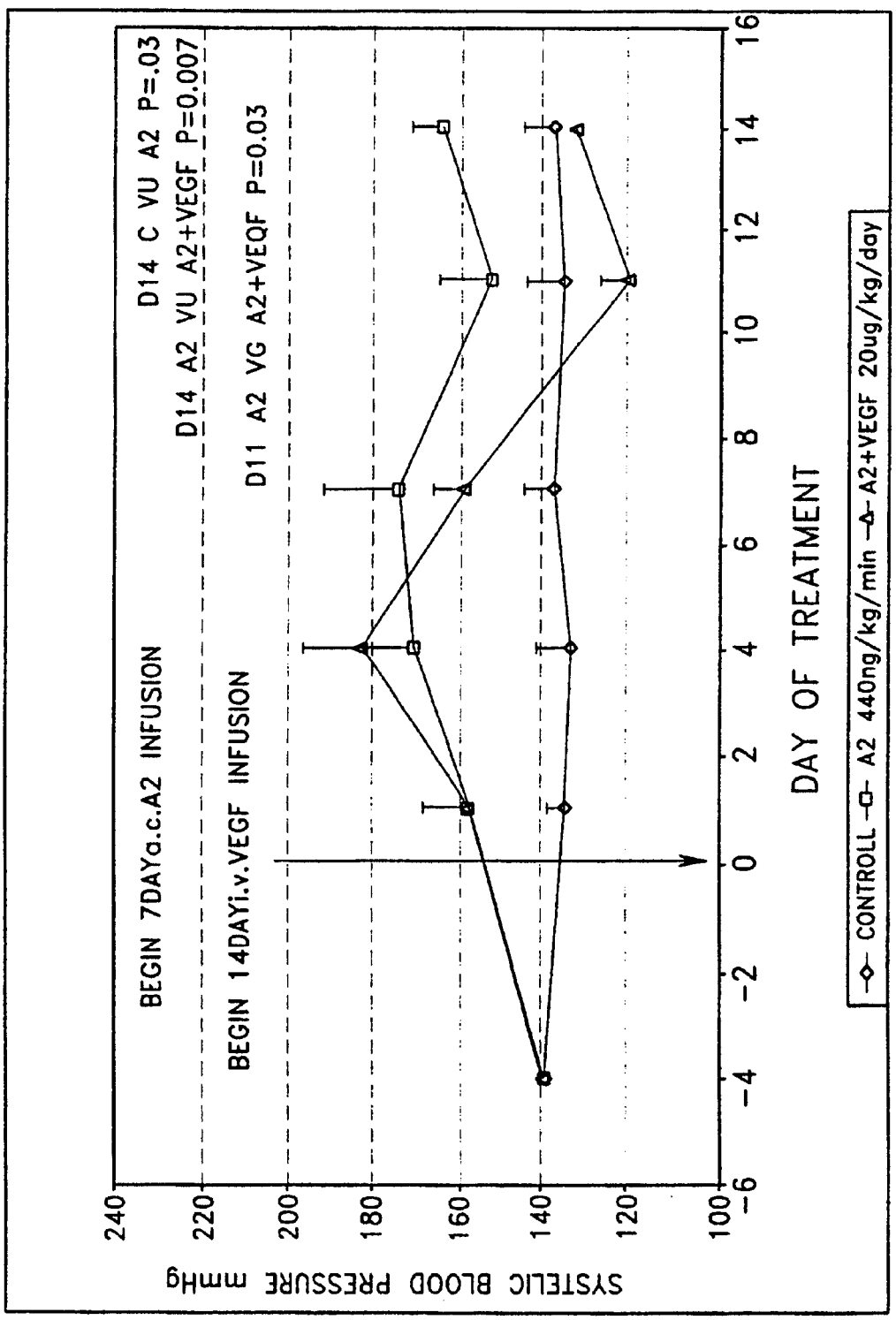
Figure 5:
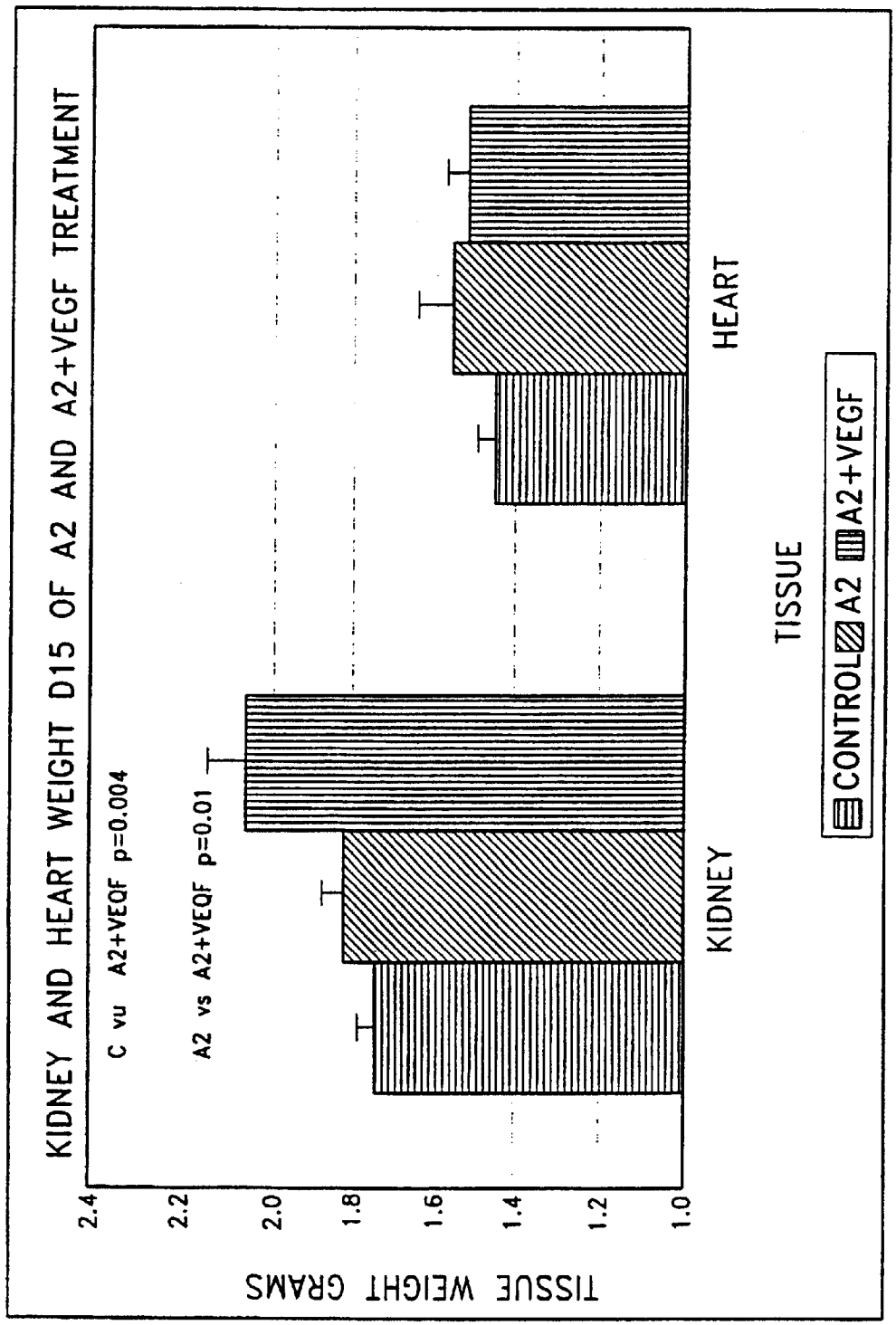
FIG. 5 depicts the weight of heart and kidney from rats treated as described in FIG. 4c.

After three days, the rats were then subjected to continuous intravenous infusion of angiotensin II (AII) at 200 ng/kg/min for 1–2 weeks. As shown in FIG. 4b, all AII-treated animals developed systolic hypertension. If the rats were on a low salt diet throughout, the blood pressure rapidly normalized. If the animals were placed on a high salt diet, the blood pressure remained elevated after the cessation of AII infusion, demonstrating a form of salt-dependent hypertension. As shown in FIG. 4c, if rats received $VEGF_{121}$ at 20 μg/kg/day for 14 days concurrent with a 7 day infusion of AII, both groups were comparable with respect to initial elevation in blood pressure. Both sets of rats were fed a high-salt diet. Upon cessation of AII however, systolic blood pressure in the animals additionally treated with VEGF drops to normal or below-normal levels, while the systolic blood pressure of the animals receiving a transient exposure to AII remained elevated. Comparison of organ within these animal groups demonstrated that the kidneys of animals treated with VEGF demonstrate marked hypertrophy, while those exposed to high salt or high salt plus AII infusions did not (FIG. 5). This unexpected result demonstrates that angiogenic stimulation facilitates the hypertrophy of the kidney to adapt to the filtration demands imposed by high salt diet and a preceding or concurrent state of hypertension.

EXAMPLE 3

Treatment of Salt-sensitive Hypertension Induced by Transient Angiotensin II (AII) Generation, with hVEGF$_{121}$ Laboratory rats (Sprague-Dawley males, weighing 300 grams) on a high salt diet (4% NaCl) received a continuous infusion of angiotension II (AII) (444 ng/kg/min, s.c.) for 7 days. The high salt diet started 3 days prior to the infusion of AII, and was continued throughout the experiment (an additional 7 days). VEGF$_{121}$ (20 µg/kg/day, i.v.) or vehicle (phosphate bufered saline) was administered during the 14 days period. The VEGF treatment did not lower the blood pressure in rats of normal salt diet or reduce the initial hypertensive response to acute AII infusion. However, blood pressure during the period following AII administration was significantly lower than in vehicle treated rats and similar to control rats on a high salt diet that had never been exposed to AII (day 14: AII/vehicle: 167±5; AII/VEGF: 136±3, high salt control: 138±5, p<0.05). VEGF infusion was also associated with increased urinary nitrite excretion (VEGF vs. vehicle, 150 vs 35 nmol/day, p<0.01), and with hypertrophy of the renal medulla.

AII infusion results in dysregulated VEGF expression with alterations in interstitial capillary structure and nitric oxide generation that predisposes rats to salt sensitive hypertension. VEGF infusion corrects the nitric oxide abnormalities and prevents the development of post AII induced hypertension.

EXAMPLE 4

VEGF$_{121}$ Reduced Blood Pressure Response to High Salt Diet in Rats with Chronic Cyclosporin Nephropathy Cyclosporin (CSA) has been associated with tubulointerstitial disease and the development of salt-sensitive hypertension. Previous study suggests that the renal vasoconstriction and injury might be mediated by a decrease in local nitric oxide concentration (*Kidney Int*. 53:897, 1998). We decided to test whether VEGF is able to prevent the development of salt-sensitive hypertension in rats with established chronic CSA nephropathy. The model was induced in laboratory rats (Sprague-Dawley males, weighing 300 grams) by subcutaneous injection of CSA (15 mg/kg/day) for 45 days, while the rats were kept on a low salt diet (0.125% NaCl). After 5 days of washout period (day 50), the diet was switched to high salt (4% NaCl) and the rats received subcutaneous injection of either VEGF$_{121}$ (100 µg/kg/day) or vehicle for 14 days. Then all treatment was discontinued for an additional 5 days and rats were sacrificed.

The VEGF-treated rats had lower blood pressure in response to a high salt diet during the post-CSA injection period, and this effect persisted even after stopping the VEGF$_{121}$ injections for 5 days. Interestingly, there was no difference in histology (light microscopy) or renal function (BUN) in the VEGF and vehicle treated rats at the end of the study. Urinary nitrates/nitrites (nitric oxide metabolites) were undetectable in the urine of VEGF and vehicle treated rats for 7 days, and were not different at sacrifice (2932±738 vs. 2516±564 nmol/day, p=NS). These data indicate that VEGF reduces the blood pressure response to high salt in rats exposed to CSA, and the effect is persistent even after VEGF administration is stopped.

EXAMPLE 5

Inhibition of Salt Sensitive Hypertension in Rats by VEGF Treatment

Figure 12:
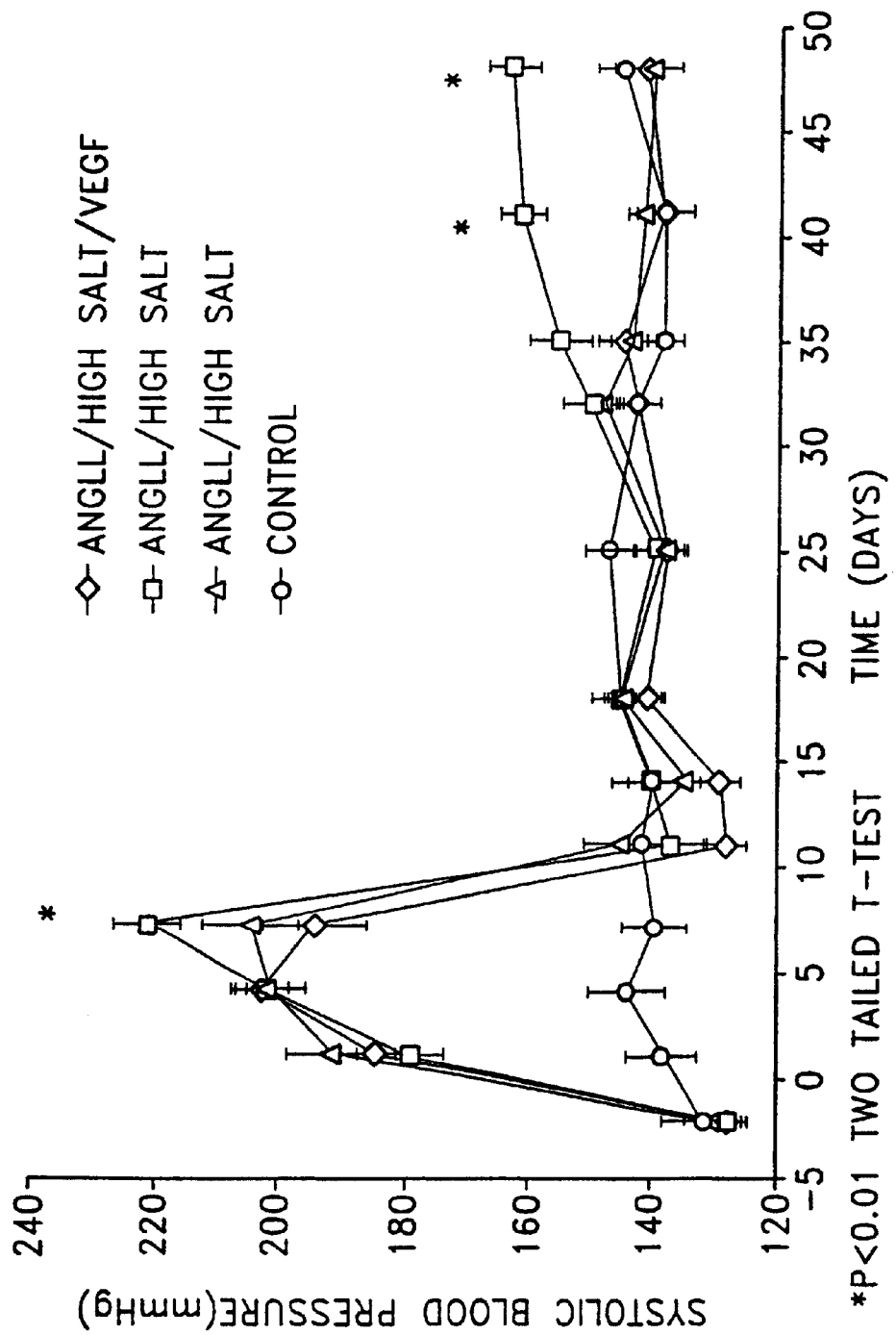
FIG. 12 illustrates the ability of VEGF treatment to inhibit the development of experimental salt sensitive hypertension in rats.

Laboratory rats (Sprague-Dawley males, 3-months of age) were divided into three treatment groups, and one control group, each group including 10 animals. Group 1 was kept on a high salt diet (4% NaCl) and received a continuous infusion (via Alzet pump) of angiotension II (AII) (440 ng/kg/min, s.c.) for 7 days. Group 2 was kept on a low salt diet (0.01% NaCl) and received a continuous infusion (via Alzet pump) of angiotension II (AII) (440 ng/kg/min, s.c.) for 7 days. Group 3 was kept on a high salt diet, just as Group 1, but also received rhVEGF$_{121}$ (100 µg/kg/day, s.q.) starting at day 0, and continuing through day 48, then stopping for observation. Group 4 (control group) received no treatment. The blood pressure of animals in all groups was measured twice weekly, at days 1, 2, 4, 7, 11, 14, 21, 25, 28, 32, 35, 41, and 48. Urine was collected at week 2 from Group 1, Group 3, and Group 4 animals (6 animals from each group) and specimen centrifuged and kept frozen for future protein, electrolytes, creatinine and urine intrates measurements. As illustrated in FIG. 12, animals in all three treatment groups showed a hypertensive response to acute AII infusion. When the AII treatment was discontinued, the blood pressure normalized but then increased again in the group kept on high salt diet in the absence of VEGF treatment (Group 1). In contrast, VEGF treatment kept the blood pressure of animals kept on high salt diet (Group 3) at normal level, demonstrating that VEGF treatment is capable of preventing the development of hypertension in this experimental model of salt sensitive hypertension.

All publications and patent applications mentioned in this specification are herein incorporated be reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for treating salt-sensitive hypertension, comprising administering to a patient suffering from salt-sensitive hypertension a vascular endothelial growth factor (VEGF) in an amount effective to reduce blood pressure to a normal range.

2. The method of claim 1 wherein said VEGF is selected from the group consisting of native hVEGF121 (FIG. 6, SEQ ID NO: 1), native hVEGF145 (FIG. 7, SEQ ID NO: 2), native hVEGF165 (FIG. 8, SEQ ID NO: 3), native hVEGF189 (FIG. 9, SEQ ID NO: 4), and native hVEGF206 (FIG. 10, SEQ ID NO: 5).

3. The method of claim 3 wherein said VEGF lacks the ability to bind heparin.

4. The method of claim 3 wherein said VEGF is a native hVEGF121 (FIG. 6, SEQ ID NO: 1).

5. The method of claim 3 wherein said VEGF comprises a heparin-binding domain modified to render it incapable of binding heparin.

6. The method of claim 3 wherein said VEGF comprises an amino acid alteration within its heparin-binding domain.

7. The method of claim 1 comprising the administration of two or more VEGFs.

8. The method of claim 1 wherein said VEGF is coadministered with another angiogenic factor.

* * * * *

UNITED STATES PATENT AND TRADEMARK OFFICE
CERTIFICATE OF CORRECTION

PATENT NO. : 6,352,975 B1 Page 1 of 1
DATED : March 5, 2002
INVENTOR(S) : Schreiner et al.

It is certified that error appears in the above-identified patent and that said Letters Patent is hereby corrected as shown below:

Title page,
Title, please remove the words "AND COMPOSITIONS FOR USE THEREIN"

Column 1,
Line 19, please add the following paragraph and heading before the heading entitled, "Background of the Invention."

-- STATEMENT OF GOVERNMENT INTEREST
    This invention was made with government support under NIDDK DK52121 awarded by the National Institutes of Health. The government has certain rights in the invention. --

Column 35,
Line 48, please replace "claim 3" with -- claim 1 --

Signed and Sealed this

Twenty-second Day of October, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.    : 6,352,975 B1
DATED         : March 5, 2002
INVENTOR(S)   : Schreiner et al.

It is certified that error appears in the above-identified patent and that said Letters Patent is hereby corrected as shown below:

Title page,
Item [73], Assignee add, "University of Washington, Seattle, WA"

Signed and Sealed this

Twenty-fifth Day of February, 2003

JAMES E. ROGAN
*Director of the United States Patent and Trademark Office*

SEQUENCE LISTING

<160> NUMBER OF SEQ ID NOS: 11

<210> SEQ ID NO 1
<211> LENGTH: 147
<212> TYPE: PRT
<213> ORGANISM: Homo Sapiens

<400> SEQUENCE: 1

Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
             20                  25                  30

Gly Gly Gln Asn His His Glu Val Val Lys Phe Met Asp Val Tyr Gln
         35                  40                  45

Arg Ser Tyr Cys His Pro Ile Glu Thr Leu Val Asp Ile Phe Gln Glu
     50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Cys Asp Lys
    130                 135                 140

Pro Arg Arg
145

<210> SEQ ID NO 2
<211> LENGTH: 145
<212> TYPE: PRT
<213> ORGANISM: Homo Sapiens

<400> SEQUENCE: 2

Ala Pro Met Ala Glu Gly Gly Gly Gln Asn His His Glu Val Val Lys
 1               5                  10                  15

Phe Met Asp Val Tyr Gln Arg Ser Tyr Cys His Pro Ile Glu Thr Leu
             20                  25                  30

Val Asp Ile Phe Gln Glu Tyr Pro Asp Glu Ile Glu Tyr Ile Phe Lys
         35                  40                  45

Pro Ser Cys Val Pro Leu Met Arg Cys Gly Gly Cys Cys Asn Asp Glu
     50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                 85                  90                  95

Leu Gln His Asn Lys Cys Glu Cys Arg Pro Lys Lys Asp Arg Ala Arg
            100                 105                 110

Gln Glu Lys Lys Ser Val Arg Gly Lys Gly Lys Gly Gln Lys Arg Lys
        115                 120                 125

Arg Lys Lys Ser Arg Tyr Lys Ser Trp Ser Val Cys Asp Lys Pro Arg
    130                 135                 140

Arg
145

<210> SEQ ID NO 3
<211> LENGTH: 191
<212> TYPE: PRT
<213> ORGANISM: Homo Sapiens

<400> SEQUENCE: 3

Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190

<210> SEQ ID NO 4
<211> LENGTH: 108
<212> TYPE: PRT
<213> ORGANISM: Homo Sapiens

<400> SEQUENCE: 4

Met Phe Leu Trp His Ser Ala Leu Tyr His Ala Trp Gln Ala Met Glu
 1               5                  10                  15

Gly Gln His Glu Val Phe Asp Tyr Arg Tyr His Ile Thr Val Ile Gln
                20                  25                  30

Tyr Asp Ile Tyr Phe Pro Cys Pro Met Cys Gly Cys Asp Gly Glu Val
            35                  40                  45

Thr Glu Asn Thr Gln Met Ile Pro Gln Gln Ile Glu Ser Leu His Lys
50                  55                  60

Glu Arg Lys Asp Ala Gln Lys Ser Arg Lys Lys Gln Arg Arg Lys Arg
65                  70                  75                  80

Lys Trp Val Cys Pro Ser Arg Lys Leu Val Asp Gln Cys Cys Cys Asn
                85                  90                  95

Asp Arg Lys Arg Leu Leu Glu Thr Arg Asp Pro Arg
            100                 105

<210> SEQ ID NO 5
<211> LENGTH: 116
<212> TYPE: PRT
<213> ORGANISM: Homo Sapiens

<400> SEQUENCE: 5

| Met | Phe | Leu | Trp | His | Ser | Ala | Leu | Tyr | His | Ala | Trp | Gln | Ala | Met | Glu |
| --- | --- | --- | --- | --- | --- | --- | --- | --- | --- | --- | --- | --- | --- | --- | --- |
| 1 | | | | 5 | | | | | 10 | | | | | 15 | |

Gly Gln His Glu Val Phe Asp Tyr Arg Tyr His Ile Thr Val Ile Gln
           20                25               30

Tyr Asp Ile Tyr Phe Pro Cys Pro Met Cys Gly Cys Asp Gly Glu Val
        35                40              45

Thr Glu Asn Thr Gln Met Ile Pro Gln Gln Ile Glu Ser Leu His Lys
    50                  55                60

Glu Arg Lys Asp Ala Gln Lys Ser Arg Lys Lys Gln Arg Arg Lys Arg
65                70                75              80

Lys Trp Val Val Ala Cys Leu Pro Ser Pro Pro Gly Cys Glu Arg
           85                90              95

His Phe Gln Pro Thr Lys Ser Lys Thr Ser Cys Ala Gly Glu Asn Arg
        100               105            110

Cys Cys Lys Arg
        115

<210> SEQ ID NO 6
<211> LENGTH: 444
<212> TYPE: DNA
<213> ORGANISM: Homo Sapiens

<400> SEQUENCE: 6

```
atgaactttc tgctgtcttg ggtgcattgg agccttgcct tgctgctcta cctccaccat     60
gccaagtggt cccaggctgc acccatggca gaaggaggag gcagaatca tcacgaagtg    120
gtgaagttca tggatgtcta tcagcgcagc tactgccatc caatcgagac cctggtggac    180
atcttccagg agtaccctga tgagatcgag tacatcttca agccatcctg tgtgcccctg    240
atgcgatgcg ggggctgctg caatgacgag ggcctggagt gtgtgcccac tgaggagtcc    300
aacatcacca tgcagattat gcggatcaaa cctcaccaag gccagcacat aggagagatg    360
agcttcctac agcacaacaa atgtgaatgc agaccaaaga aagatagagc aagacaagaa    420
aaatgtgaca agccgaggcg gtga                                           444
```

<210> SEQ ID NO 7
<211> LENGTH: 516
<212> TYPE: DNA
<213> ORGANISM: Homo Sapiens

<400> SEQUENCE: 7

```
atgaactttc tgctgtcttg gtggattgg agccttgcct tgctgctcta cctccaccat      60
gccaagtggt cccaggctgc acccatggca gaaggaggag gcagaatca tcacgaagtg    120
gtgaagttca tggatgtcta tcagcgcagc tactgccatc caatcgagac cctggtggac    180
atcttccagg agtaccctga tgagatcgag tacatcttca agccatcctg tgtgcccctg    240
atgcgatgcg ggggctgctg caatgacgag ggcctggagt gtgtgcccac tgaggagtcc    300
aacatcacca tgcagattat gcggatcaaa cctcaccaag gccagcacat aggagagatg    360
agcttcctac agcacaacaa atgtgaatgc agaccaaaga aagatagagc aagacaagaa    420
aaaaaatcag ttcgaggaaa gggaaagggg caaaaacgaa agcgcaagaa atcccggtat    480
aagtcctgga gcgtatgtga caagccgagg cggtga                              516
```

<210> SEQ ID NO 8

-continued

```
<211> LENGTH: 576
<212> TYPE: DNA
<213> ORGANISM: Homo Sapiens

<400> SEQUENCE: 8
atgaactttc tgctgtcttg ggtgcattgg agcctcgcct tgctgctcta cctccaccat      60
gccaagtggt cccaggctgc acccatggca gaaggaggag ggcagaatca tcacgaagtg     120
gtgaagttca tggatgtcta tcagcgcagc tactgccatc caatcgagac cctggtggac     180
atcttccagg agtaccctga tgagatcgag tacatcttca agccatcctg tgtgccctg      240 atgcgatgcg ggggctgctg caatgacgag ggcctggagt gtgtgcccac tgaggagtcc     300
aacatcacca tgcagattat gcggatcaaa cctcaccaag gccagcacat aggagagatg     360
agcttcctac agcacaacaa atgtgaatgc agaccaaaga agatagagc aagacaagaa      420 aatccctgtg ggccttgctc agagcggaga aagcatttgt ttgtacaaga tccgcagacg     480
tgtaaatgtt cctgcaaaaa cacagactcg cgttgcaagg cgaggcagct tgagttaaac     540
gaacgtactt gcagatgtga aagccgagg cggtga                                576

<210> SEQ ID NO 9
<211> LENGTH: 642
<212> TYPE: DNA
<213> ORGANISM: Homo Sapiens

<400> SEQUENCE: 9
atgaactttc tgctgtcttg ggtgcattgg agcctcgcct tgctgctcta cctccaccat      60
gccaagtggt cccaggctgc acccatggca gaaggaggag ggcagaatca tcacgaagtg     120
gtgaagttca tggatgtcta tcagcgcagc tactgccatc caatcgagac cctggtggac     180
atcttccagg agtaccctga tgagatcgag tacatcttca agccatcctg tgtgccctg      240 atgcgatgcg ggggctgctg caatgacgag ggcctggagt gtgtgcccac tgaggagtcc     300
aacatcacca tgcagattat gcggatcaaa cctcaccaag gccagcacat aggagagatg     360
agcttcctac agcacaacaa atgtgaatgc agaccaaaga agatagagc aagacaagaa      420 aaaaaatcag ttcgaggaaa gggaaggggg caaaaacgaa agcgcaagaa atcccggtat     480
aagtcctgga gcgtggggcc ttgctcagag cggagaaagc atttgtttgt acaagatccg     540
cagacgtgta aatgttcctg caaaaacaca gactcgcgtt gcaaggcgag gcagcttgag     600
ttaaacgaac gtacttgcag atgtgacaag ccgaggcggt ga                         642

<210> SEQ ID NO 10
<211> LENGTH: 699
<212> TYPE: DNA
<213> ORGANISM: Homo Sapiens

<400> SEQUENCE: 10
atgaactttc tgctgtcttg ggtgcattgg agcctcgcct tgctgctcta cctccaccat      60
gccaagtggt cccaggctgc acccatggca gaaggaggag ggcagaatca tcacgaagtg     120
gtgaagttca tggatgtcta tcagcgcagc tactgccatc caatcgagac cctggtggac     180
atcttccagg agtaccctga tgagatcgag tacatcttca agccatcctg tgtgccctg      240 atgcgatgcg ggggctgctg caatgacgag ggcctggagt gtgtgcccac tgaggagtcc     300
aacatcacca tgcagattat gcggatcaaa cctcaccaag gccagcacat aggagagatg     360
agcttcctac agcacaacaa atgtgaatgc agaccaaaga agatagagc aagacaagaa      420 aaaaaatcag ttcgaggaaa gggaaggggg caaaaacgaa agcgcaagaa atcccggtat     480
```

```
aagtcctgga gcgtgtacgt tggtgcccgc tgctgtctaa tgccctggag cctccctggc     540
ccccatccct gtgggccttg ctcagagcgg agaaagcatt tgtttgtaca agatccgcag     600
acgtgtaaat gttcctgcaa aaacacagac tcgcgttgca aggcgaggca gcttgagtta     660
aacgaacgta cttgcagatg tgacaagccg aggcggtga                           699
```

<210> SEQ ID NO 11
<211> LENGTH: 110
<212> TYPE: PRT
<213> ORGANISM: Homo Sapiens

<400> SEQUENCE: 11

```
Ala Pro Met Ala Glu Gly Gly Gly Gln Asn His His Glu Val Val Lys
 1               5                  10                  15

Phe Met Asp Val Tyr Gln Arg Ser Tyr Cys His Pro Ile Glu Thr Leu
                20                  25                  30

Val Asp Ile Phe Gln Glu Tyr Pro Asp Glu Ile Glu Tyr Ile Phe Lys
             35                  40                  45

Pro Ser Cys Val Pro Leu Met Arg Cys Gly Gly Cys Cys Asn Asp Glu
         50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg
                100                 105                 110
```